US009630897B2

(12) United States Patent
Chisholm et al.

(10) Patent No.: US 9,630,897 B2
(45) Date of Patent: Apr. 25, 2017

(54) MONOMERS AND POLYMERS DERIVED FROM NATURAL PHENOLS

(71) Applicants: Bret Ja Chisholm, West Fargo, ND (US); Samim Alam, Tarrytown, NY (US)

(72) Inventors: Bret Ja Chisholm, West Fargo, ND (US); Samim Alam, Tarrytown, NY (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 14/774,628

(22) PCT Filed: Mar. 11, 2014

(86) PCT No.: PCT/US2014/023181
§ 371 (c)(1),
(2) Date: Sep. 10, 2015

(87) PCT Pub. No.: WO2014/197041
PCT Pub. Date: Dec. 11, 2014

(65) Prior Publication Data
US 2016/0023980 A1   Jan. 28, 2016

Related U.S. Application Data

(60) Provisional application No. 61/776,362, filed on Mar. 11, 2013.

(51) Int. Cl.

| | | |
|---|---|---|
| C07C 67/04 | (2006.01) | |
| C07C 43/215 | (2006.01) | |
| C08F 16/32 | (2006.01) | |
| C08F 24/00 | (2006.01) | |
| C08F 14/14 | (2006.01) | |
| C08F 16/38 | (2006.01) | |
| C08F 16/08 | (2006.01) | |
| C07C 43/205 | (2006.01) | |
| C08F 216/12 | (2006.01) | |
| C07C 67/24 | (2006.01) | |
| C07C 69/007 | (2006.01) | |
| C08F 116/38 | (2006.01) | |
| C08F 216/38 | (2006.01) | |
| C08F 216/08 | (2006.01) | |
| C08F 116/08 | (2006.01) | |

(52) U.S. Cl.
CPC ........ C07C 43/215 (2013.01); C07C 43/2055 (2013.01); C07C 67/24 (2013.01); C07C 69/007 (2013.01); C08F 14/14 (2013.01); C08F 16/08 (2013.01); C08F 16/32 (2013.01); C08F 16/38 (2013.01); C08F 24/00 (2013.01); C08F 216/125 (2013.01); C08F 116/08 (2013.01); C08F 116/38 (2013.01); C08F 216/08 (2013.01); C08F 216/38 (2013.01); C08F 2216/085 (2013.01)

(58) Field of Classification Search
CPC ... C07C 43/215; C07C 43/2005; C07C 67/24; C08F 16/38; C08F 16/08; C08F 116/08; C08F 116/38; C08F 216/08; C08F 216/38; C08F 2216/08; C08F 2216/085
See application file for complete search history.

(56) References Cited

U.S. PATENT DOCUMENTS

| | | | |
|---|---|---|---|
| 2,335,651 | A | 11/1943 | D'Alelio |
| 3,928,388 | A | 12/1975 | Reichenbacher |
| 4,617,238 | A * | 10/1986 | Crivello ................. C08G 77/38 428/447 |
| 5,070,117 | A | 12/1991 | Klemarczyk et al. |
| 8,785,582 | B2 | 7/2014 | Hojo et al. |
| 2008/0174051 | A1 | 7/2008 | DiPietro et al. |
| 2012/0316309 | A1 | 12/2012 | Chisholm et al. |
| 2013/0245189 | A1 | 9/2013 | Hojo et al. |
| 2014/0296444 | A1 | 10/2014 | Chisholm et al. |

FOREIGN PATENT DOCUMENTS

| | | |
|---|---|---|
| EP | 0 463 862 A2 | 1/1992 |
| WO | WO 98/28339 A1 | 7/1998 |
| WO | WO 02/16516 A1 | 2/2002 |
| WO | WO 2006/024885 A1 | 3/2006 |
| WO | WO 2007/088126 A2 | 8/2007 |
| WO | WO 2010/035903 A1 | 4/2010 |
| WO | WO 2011/060293 A1 | 5/2011 |
| WO | WO 2011/069111 A1 | 6/2011 |
| WO | WO 2014/197041 A2 | 12/2014 |
| WO | WO 2014/197041 A3 | 1/2015 |
| WO | WO 2014/197041 A8 | 3/2015 |

OTHER PUBLICATIONS

Alam, "Synethesis and characterization of novel polyvinylether polymers produced using carbocationic polymerization," Doctoral Dissertation; North Dakota State University; Fargo, ND, Publication date Jun. 20, 2012.*
Alam, "Synethesis and characterization of novel polyvinylether polymers produced using carbocationic polymerization," Abstract from Doctoral Dissertation; North Dakota State University; Fargo, ND. Publication date Jun. 20, 2012 [retrieved on Nov. 19, 2015]. Retrieved from the Internet:<URL:http://search.proquest.com/docview/1009735432 >; 3 pgs.
Grant abstract from Grant No. IIA-1330840 awarded by the National Science Foundation, Aug. 1, 2013, 1 page.
Office Action mailed Jan. 21, 2016, in U.S. Appl. No. 14/204,102.
Notice of Allowance mailed Jun. 8, 2016, in U.S. Appl. No. 14/204,102.

(Continued)

*Primary Examiner* — Ling Choi
*Assistant Examiner* — David L Miller
(74) *Attorney, Agent, or Firm* — Mueting, Raasch & Gebhardt, P.A.

(57) ABSTRACT

Monomers, polymers and copolymers are provided that incorporate at least one naturally occurring phenolic compound, such as a plant phenol.

6 Claims, 3 Drawing Sheets

(56) References Cited

OTHER PUBLICATIONS

Alam et al., "Coatings derived from novel, soybean oil-based polymers produced using carbocationic polymerization," *J. Coat. Technol. Res.*, 2011; 8:671-683.
Alam et al., "Novel Multifunctional Bio-based Polymers for Coating Applications," Slides accompanying oral presentation at the *ACA CoatingsTech Conference* (American Coatings Association): Chicago, IL; Mar. 12, 2013.
Alam et al., "Soy-Based Surface Active Copolymers As a Safer Replacement for Low Molecular Weight Surfactants," *ACS Sustainable Chem. Eng.*, 2013; 1:-19-22. Availale online Oct. 4, 2012.
Alam et al., "Novel Bio-Based Epoxy Resins," Slides accompanying oral presentation on Apr. 10, 2013, at the *245th ACS National Meeting—Division of Natural and Renewable Polymers* (American Chemical Society): New Orleans, LA; Apr. 10, 2013.
Alam et al., "Novel Bio-Based Epoxy Resins," Abstract No. 251 accompanying oral presentation on Apr. 10, 2013, at the *245th ACS National Meeting—Division of Natural and Renewable Polymers* (American Chemical Society): New Orleans, LA; Apr. 7-11, 2013.
Alam et al., "2-(Vinyloxy)ethyl soyate as a versatile platform chemical for coatings: An overview," *Eur. J. Lipid Sci. Technol,.* 2014; 116:2-15. Available online Sep. 19, 2013.
Aoshima et al., "Living cationic polymerization of vinyl monomers by organoaluminum halides. 3. Living polymerization of isobutyl vinyl ether by ethyldichloroaluminum in the presence of ester additives," *Macromolecules*, 1989; 22(3):1009-1013.
Aoshima et al., "New stage in living cationic polymerization: An array of effective Lewis acid catalysts and fast living polymerization in seconds," *J. Polym. Sci. Part A: Polym. Chem. Ed.*, Mar. 2007; 45:1801-1813.
Aoshima et al., "A Renaissance in Living Cationic Polymerization," *Chem. Rev.*, Oct. 5, 2009; 109(11):5245-5287.
Balachandran et al., "Recent advances in cardanol chemistry in a nutshell: from a nut to nanomaterials," *Chem. Soc. Rev.*, 2013; 42:427-438. Available online Nov. 1, 2012.
Braun et al., "Polymers from non-homopolymerizable monomers by free radical processes," *Prog. Polymer Sci.*, 2006; 31:239-276.
Chernykh et al., "Living carbocationic polymerization of a vinyl ether monomer derived from soybean oil, 2-(vinyloxy)ethyl soyate," *Green Chemistry*, 2013; 7:1834-1838. Published online May 10, 2013.
Chishom et al., Final Report, Grant No. ONR N00014-06-1-0952 awarded by the Office of Naval Research, Report No. CNSE-08-03. Mar. 2008; 326 pages.
Chisholm, "Bio-Based Polyvinyl Ethers for Coating Applications," Abstract, *2013 CoatingsTech Conference*; Mar. 11-13, 2013. 1 page.
Chisholm, "Novel Soybean Oil-Derived Acrylates for UV-Curable Coatings," Manuscript for Roon Award, *2013 CoatingsTech Conference*; Mar. 11-13, 2013. 31 pages.
Emter et al., "Performance of a novel keratinocyte-based reporter cell line to screen skin sensitizers in vitro," *Toxicology and Applied Pharmacology*, Jun. 2010; 245(3):281-290.
Kalita et al., "Bio-based poly(vinyl ether)s and their application as alkyd-type surface coatings," *Green Chemistry*, 2014; 16:1974-1986. Available online Jan. 10, 2014.
Kanazawa et al., "Major Progress in Catalysts for Living Cationic Polymerization of Isobutyl Vinyl Ether: Effectiveness of a Variety of Conventional Metal Halides," *Macromolecules*, 2009; 42:3965-3972.
Kibet et al., "Molecular Products and Radicals from Pyrolysis of Lignin," *Environ. Sci. Technol.*, Dec. 4, 2012; 46:12994-13001. Available online Nov. 6, 2012.
Kuroda et al., "Analytical pyrolysis of lignin: Products stemming from β-5 substructures," *Organic Geochemistry*, Jun. 2006; 37:665-673. Available online Apr. 27, 2006.
Li et al., "Application of the Random Forest Method in Studies of Local Lymph Node Assay Based Skin Sensitization Data," *Journal of Chemical Information and Modeling*, 2005; 45(4):952-964.
Lichtenthaler et al., "Carbohydrates as green raw materials for the chemical industry," *C.R. Chimie*, Feb. 2004; 7(2):65-90.
Miyamoto et al., "Living Polymerization of Isobutyl Vinyl Ether with the Hydrogen Iodide/Iodine Initiating System," *Macromolecules*, Mar. 1984; 17(3):265-268.
Natsch et al., "LC-MS-Based Characterization of the Peptide Reactivity of Chemicals to Improve the In Vitro Prediction of the Skin Sensitization Potential," *Toxicological Sciences*, 2008; 106(2):464-478.
Shen et al., "The pyrolytic degradation of wood-derived lignin from pulping process," *Bioresource Technology*, Aug. 2010; 101(15):6136-6146. Available online Mar. 21, 2010.
Stanzione et al., "Lignin Model Compounds as Bio-Based Reactive Diluents for Liquid Molding Resins," *Chem. Sus. Chem.*, 5(7):1291-1297, Apr. 19, 2012.
Yuan et al., "Preparation of the precursors of new tannin-like polymers with potential biological effects," *Die Makromolekulare Chemie*, 1992; 193(12):3037-3044.
International Search Report (from PCT/ISA/210) mailed Nov. 28, 2014, in related application PCT/US2014/023181. 4 pages.
Hashimoto et al., "Cationic Polymerization of Vinyl Ethers with a Benzoate or Phenylacetate Pendant: Synthesis of New Poly(Carboxylic Acid)s with Poly(Vinyl Ether) Backbone," *Journal of Macromolecular Science, Part A*, Jan. 1999; 36(3):449-460.

* cited by examiner

MONOMERS AND POLYMERS DERIVED FROM NATURAL PHENOLS

This application is the §371 U.S. National Stage of International Application No. PCT/US2014/023181, filed 11 Mar. 2014, which claims the benefit of U.S. Provisional Application Ser. No. 61/776,362 filed Mar. 11, 2013, each of which is incorporated herein by reference in its entirety.

STATEMENT OF GOVERNMENT RIGHTS

This invention was made with government support under Grant No. ONR N00014-06-1-0952 awarded by the Office of Naval Research, and Grant No. IIA-1330840 awarded by the National Science Foundation. The government has certain rights in the invention.

BACKGROUND

Due to the finite supply of fossil resources and societies ever increasing interest in the use of renewable resources for energy and materials, there is a major need for new chemicals and materials derived from renewable resources. With regard to polymers, aromatic building blocks are tremendously important. For example, commodity polymers such as polycarbonate and polyethylene terephthalate are based on aromatic monomers. While many renewable resources such as plant oils, carbohydrates, and sugars are aliphatic, there are a number of phenols that can be obtained from renewable sources. In fact, lignin, which is a complex polymer network of aromatic alcohols, known as monolignols, is one of the most abundant renewable resources on the planet. Lignin constitutes 30% of all organic carbon on the planet and 25 to 33% of the dry mass of wood.

SUMMARY OF THE INVENTION

The invention provides novel monomers and polymers derived from natural phenols, as well as methods for producing the monomers and polymers. The invention provides novel monomers and polymers derived from natural phenols, as well as methods for producing the monomers and polymers. In one aspect, the invention provides a novel vinyl ether monomer. In one embodiment, the vinyl ether monomer has the structure:

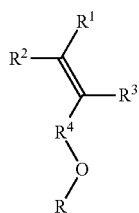

where $R_1$, $R_2$, and $R_3$ are each independently H or alkyl; $R_4$ is either —O—$R_{10}$— or absent; $R_{10}$ is divalent organic group; and R is a substituted phenyl group.

In another aspect, the invention provides a polymer or copolymer that incorporates at least one vinyl ether monomer of the invention. The vinyl ether monomer is preferably formed from, or includes, at least one naturally occurring phenolic compound, or an analog or derivative thereof. In one embodiment, the polymer or copolymer contains, as a repeating unit, the structure:

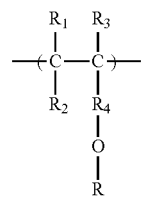

where $R_1$, $R_2$, and $R_3$ are each independently H or alkyl; $R_4$ is either —O—$R_{10}$— or absent; $R_{10}$ is divalent organic group; and R is a substituted phenyl group.

The substituted phenyl group R can be a mono-, di-, tri-, tetra-, or penta-substituted phenyl group. Preferably, at least one substituent of the phenyl group contains at least one reactive functional group. Examples of a reactive functional group include a primary, secondary or tertiary alcohol; an aldehyde; a double bond; a triple bond; a primary, secondary, tertiary or quaternary amine; an ester; a ketone; an epoxide; a carboxylic acid; or any combination thereof. In some embodiments the reactive functional group includes an epoxide group, an acrylate-functional group, an alcohol group, or any combination thereof. In a preferred embodiment of the vinyl ether monomer of the invention, the phenyl group is derived from eugenol, isoeugenol, vanillin, cardanol, cardol, or anacardic acid. In another preferred embodiment, the phenyl group is derived from a phenolic compound obtained from lignocellulose.

A preferred polymer or copolymer includes, as a repeating unit, the structure:

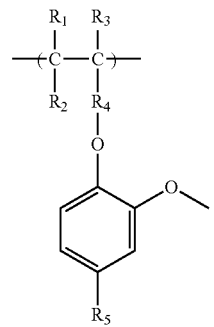

where $R_1$, $R_2$, and $R_3$ are —H or -alkyl; $R_4$ is —O-alkylene- or absent; $R_5$ is either or both of $CH_2$—CH=$CH_2$ and/or CH=CH—$CH_3$. Advantageously, the phenyl group can be derived from a phenolic compound obtained from lignocellulose. In a preferred embodiment, the polymer or copolymer includes a polyvinyl ether, such as a polyvinyl ether that includes an alkylene vinyl ether as a repeating unit. Optionally, the polyvinyl ether is epoxidized. In a preferred embodiment, the polymer or copolymer contains a repeating unit derived from 4-allyl-2-methoxy-1-(2-(vinyloxy)ethoxy) benzene (AMB). An example of a preferred polymer or copolymer is one that includes poly[4-allyl-2-methoxy-1-(2-(vinyloxy)ethoxy)benzene] (polyAMB).

In one embodiment, the copolymer of the invention can include at least one comonomer comprising an isobutyl vinyl ether, a cyclohexyl vinyl ether, a tri(ethylene glycol) ethyl vinyl ether, a penta(ethylene glycol) ethyl vinyl ether, or a combination thereof.

In another embodiment, the copolymer contains at least one comonomer comprising an electron deficient vinyl monomer, such as maleic anhydride. Optionally, the copolymer is produced by free radical polymerization. The copolymer maybe an alternating copolymer.

Optionally, the polymer or copolymer contains a cross-linked siloxane.

Optionally, the polymer or copolymer has a polydispersity index of less than 1.5.

In another aspect, the invention includes a method for making the polymer or copolymer that includes polymerizing a vinyl ether monomer of the invention with at least one comonomer under conditions to form a polymer or copolymer. In one embodiment, the comonomer includes a vinyl ether monomer, such as a penta(ethylene glycol) ethyl vinyl ether (PEGEVE), a tri(ethylene glycol) ethyl vinyl ether (TEGEVE), a cyclohexyl vinyl ether (CHVE), an isobutyl vinyl ether, or any combination thereof.

In yet another aspect, the invention includes a novel functionalized initiator compound, which is especially useful in carbocationic polymerization reactions. In one embodiment, the functionalized initiator compound is an 1-(2-(4-allyl-2-methoxyphenoxy)alkoxy)ethyl acetate, preferably 1-(2-(4-allyl-2-methoxyphenoxy)ethoxy)ethyl acetate (AMEA). Also included is a method for making the functionalized initiator compound of the invention, for example by contacting 4-allyl-2-methoxy-1-(2-(vinyloxy) alkoxy)benzene with acetic acid under conditions and for a time sufficient to yield the functionalized initiator compound 1-(2-(4-allyl-2-methoxyphenoxy)alkoxy)ethyl acetate. In a preferred embodiment of the method, 4-allyl-2-methoxy-1-(2-(vinyloxy)ethoxy)benzene is contacted with acetic acid under conditions and for a time sufficient to yield the functionalized initiator compound, 1-(2-(4-allyl-2-methoxyphenoxy)ethoxy)ethyl acetate (AMEA).

In another aspect, the invention includes a method for making a functionalized polymer or copolymer that includes contacting at least one vinyl ether monomer, including but not limited to vinyl ether monomers derived from natural phenols, with the functionalized initiator compound under conditions and for a time sufficient to yield the functionalized polymer or copolymer, wherein the functionalized polymer or copolymer includes a terminal allyl group. Optionally at least one additional monomer can be contacted with the functionalized initiator compound under conditions and for a time sufficient to yield the allyl-functionalized polymer or copolymer. The resultant allyl-functionalized polymer or copolymer can, in turn, be used to form other copolymers. For example, the allyl-functionalized polymer or copolymer can be reacted with at least one second polymer or copolymer, to yield a block or graft copolymer produced through a reaction at the terminal allyl group of the functionalized polymer or copolymer. In a preferred embodiment, the block or graft copolymer includes a poly (dimethylsiloxane) (PDMS).

In yet another aspect, the invention provides an article, coating, film, adhesive, elastomer, detergent, surfactant, composite, oil, gel or lubricant comprising the polymer or copolymer of the invention.

DETAILED DESCRIPTION OF ILLUSTRATIVE EMBODIMENTS

Figure 1:
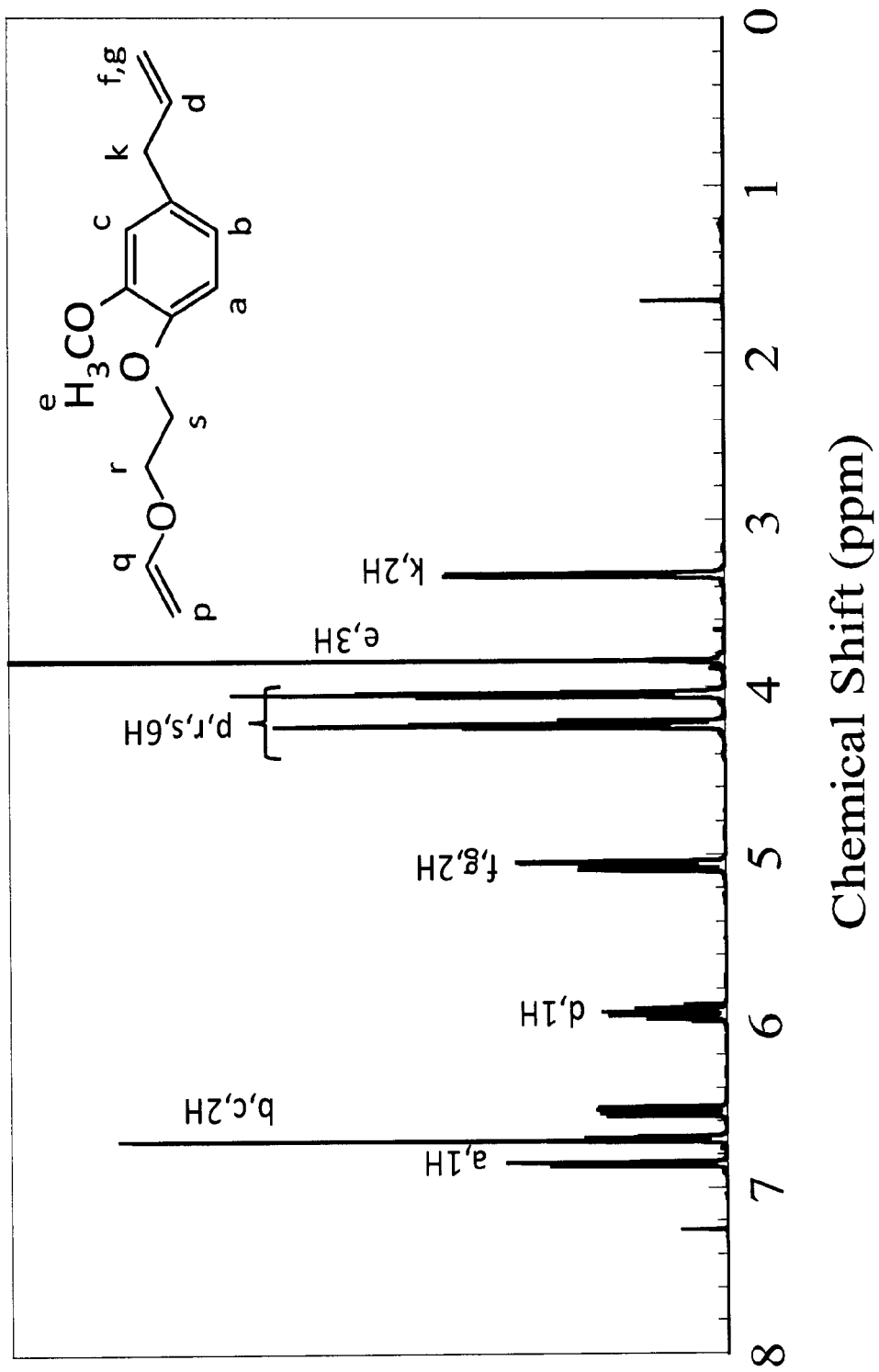
FIG. 1 shows a proton nuclear magnetic resonance spectrum (1H-NMR) for from 4-allyl-2-methoxy-1-(2-(vinyloxy)ethoxy)benzene (AMB).

The present invention provides monomers, as well as polymers and copolymers that incorporate at least one monomer, which are formed from, or include, at least one naturally occurring phenolic compound, or an analog or derivative thereof. Also included in the invention are methods for making the monomers and polymers, and methods of using them to produce lubricating liquids such as lubricants, oils, and gels, as well as coatings, films, adhesives, elastomers, detergents, surfactants, composite materials, and the like. Articles, coatings, films, adhesives, elastomers, detergents, surfactants, composites, oils, gels and lubricants that include monomers or polymers of the invention, cured or uncured, as well as methods for making and using them, are also provided by the invention.

The naturally occurring phenolic compound is preferably a phenolic compound that is found naturally in a plant. Such compounds are also known as natural phenols, plant phenolics or plant phenols. The phenolic compound used to make the monomer or polymer of the invention can be isolated from a plant or a plant material (or other living organism), or it can be chemically or enzymatically synthesized. Plant material includes material that is or was part of a plant, as well as material that is produced as a result of degradation of the plant or a plant part, for example by hydrolysis, proteolysis, or pyrolysis. Monomers and polymers that incorporate a phenolic compound isolated from a plant, plant material or other living organism make use of renewable resources and can thus be categorized as "green" products and technologies. While the naturally occurring phenolic compounds useful in the invention are commonly found in plants, suitable phenolic compounds can also be found in other living organisms such as microorganisms, including fungi, and also insects and mammals, for example.

A phenol includes a hydroxyl group (—OH) as a first ring substituent attached to the phenyl ring. The monomers of the present invention are synthesized via reaction at the phenolic hydroxyl/phenolate group. Phenols that are useful as starting materials in the synthesis of monomers according to the present invention preferably contain at least a second ring substituent that is, or contains, a reactive functional group. This reactive functional group is in addition to the hydroxyl group. The phenolic compounds useful in the invention can thus be characterized as substituted phenols. Ring substituents (in addition to the phenolic hydroxyl) can contain one or more reactive functional groups, including but not limited to: a primary, secondary or tertiary alcohol; an aldehyde; a double bond (including but not limited to vinyl group or an allyl group); a triple bond; a primary, secondary, tertiary or quaternary amine; an ester; a ketone; an epoxide, and/or a carboxylic acid. A reactive functional group supplies a site that permits further modification or derivatization of the monomer, or the polymer into which it is incorporated. A functional group that can be derivatized in this manner, under suitable or defined reaction conditions, is referred to herein as a reactive functional group.

Optionally, a substituted phenol includes two or more additional ring substituents (i.e., substituents at two or more positions on the ring in addition to the phenolic hydroxyl, for example, second and third substituents). Each additional ring substituent optionally, and independently, contains a reactive functional group, which can be the same or different. Alternatively or in addition, an additional ring substituent is optionally a multifunctional substituent. A multifunctional substituent optionally contains more than one reactive functional group, such as both a double bond and a hydroxyl, or both a double bond and an aldehyde. A phenolic compound that contains at least one reactive functional group in addition to the phenolic hydroxyl is referred to herein as a "functionalized" phenolic compound or a "functionalized" phenol, and is a preferred starting material for synthesizing the monomer of the invention. It should be understood that the reactive functional group(s) can be part or the naturally occurring phenol, or can be added chemically or enzymatically.

Plant Phenols

Phenolic compounds for use as starting materials in the synthesis of the monomers of the invention can be isolated from any suitable plant or plant material. As a nonlimiting example, the phenolic compounds eugenol and isoeugenol, which contain a reactive allyl group and a reactive disubstituted (—C=C—) double bond, respectively, are suitable starting materials that can be isolated from clove oil.

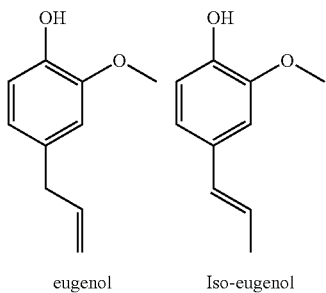

eugenol   Iso-eugenol

Eugenol and isoeugenol can also be obtained as products of the degradation of lignin, for example, by pyrolysis. More generally, many suitable plant phenols can be obtained from biomass such as lignocellulose, or degradation products thereof, including but not limited to p-coumaryl alcohol, coniferyl alcohol, sinapyl alcohol, 4-vinylguaiacol, 4-propenylsyringol, vanillin, vanillic acid, acetoguaiacone, coniferaldehyde and sinapaldehyde. Aromatic alcohols derived from lignin or lignocellulose, known as monolignols, are particularly preferred plant phenols for use as starting materials for synthesis of the monomers and polymers of the invention.

Other suitable plant phenols for use as starting materials in the synthesis of the monomers of the invention include those found in cashew nutshell liquid. Cashew nutshell liquid (CNSL) is a renewable biomaterial extracted from the soft honeycomb structure inside the cashew nutshell. Naturally occurring components of CNSL include phenolic compounds such as anacardic acid, cardol, cardanol, 2-methyl cardol or cardanol, and 6-methyl cardol or cardanol. The structures of cardol, anacardic acid, and cardanol are shown below, where R is a linear saturated, monounsaturated, or polyunsaturated aliphatic side chain, for example $R=C_{15}H_{31-n}$ where $n=0, 2, 4, 6$.

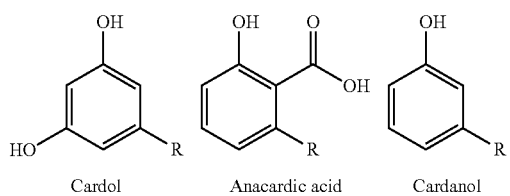

Cardol   Anacardic acid   Cardanol

Cardanol can also be produced commercially from the decarboxylation of anacardic acid. Cardanols thus include the various decarboxylated derivatives obtained by thermal decomposition of any of the naturally occurring anacardic acids. The term "cardanol" thus includes more than one compound because the composition of the side chain varies in its degree of unsaturation. Tri-unsaturated cardanol, the major component (41%), is shown below. The remaining cardanol is 34% mono-unsaturated, 22% bi-unsaturated, and 2% saturated. Cardanol is available in several forms from Cardolite, Inc. An exemplary cardanol is 3-n-pentadecadienyl phenol.

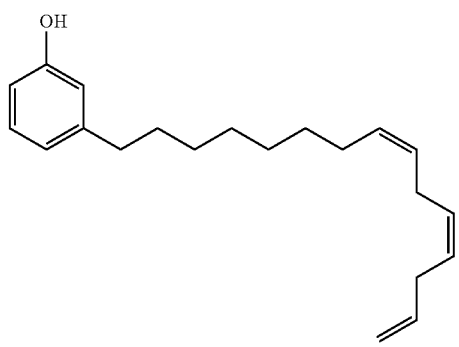 [SMILES: C=CC/C=C\C/C=C\CCCCCCCc1cccc(O)c1]

These CNSL compounds have at least one phenolic group and possess an alkyl chain meta to the phenolic group. The long aliphatic side chain provides excellent water resistance, good flexibility and low viscosity. The unsaturated C=C bonds permit subsequent optional activation or functionalization (e.g., epoxidation and acrylation) so as to facilitate crosslinking later, during the curing process, if desired. Examples of an epoxidized cardanol (ECL) useful as a reactant in the method of the invention include Cardolite® NC 513 or NC 2513, available from Cardolite, Inc. Typically UV curing is utilized, but the material can also be thermally cured or cured via an auto-oxidation process or by reaction with multi-functional thiols under elevated temperatures.

More generally, plant phenols possessing a reactive group in addition to the phenolic group, such as a double bond, aldehyde, ester, alcohol or carboxylic acid, are particularly useful.

Plant phenols, or a phenolic fraction, can be recovered from bio-oils such as pyrolysis oil and used as starting material in the reaction to yield the monomers of the invention.

Monomers

In one embodiment, the monomer of the invention is a functionalized vinyl ether monomer having the following general structure:

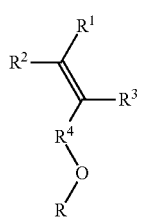

where $R_1$, $R_2$, and $R_3$ are each independently H or alkyl, preferably H or $CH_3$; $R_4$ is either —O—$R_{10}$— or absent; $R_{10}$ is divalent organic group, preferably an alkylene, that functions as a spacer between the vinyl ether and the phenyl group, R; and wherein R is a substituted phenyl group derived from a phenolic compound, preferably a plant phenol, more preferably a functionalized plant phenol. R is a mono-, di-, tri-, tetra-, or penta-substituted phenyl group; in other words, the oxygen from the phenolic hydroxyl is at ring position C-1, and the phenyl ring is substituted at one or more of ring positions C-2, C-3, C-4, C-5 and/or C-6. At least one substituent of the phenyl ring contains at least one reactive functional group such as, without limitation, a primary, secondary or tertiary alcohol; an aldehyde; a double bond (including but not limited to a vinyl group or an allyl group); a triple bond; a primary, secondary, tertiary or quaternary amine; an ester; a ketone; an epoxide, and/or a carboxylic acid. As noted herein, a ring substituent can be monofunctional or multifunctional.

A vinyl ether monomer of the invention that contains a functionalized phenolic constituent can be synthesized by reacting a vinyl ether (or a vinyl acetate) with the phenolate of a functionalized phenol to yield a functionalized vinyl ether monomer. Any vinyl ether is suitable, or can be readily made suitable, for reaction with the functionalized phenol, as desired for the intended application. In order to react with the phenolic hydroxyl of the functionalized phenol, the vinyl ether reactant preferably contains an electrophilic group or region that is susceptible to nucleophilic attack by the phenolic hydroxyl or its phenolate anion. The vinyl ether reactant can be, for example, an alkyl halide, such as chloroethyl vinyl ether or iodoethyl vinyl ether, and the reaction can take place via a nucleophilic displacement reaction under basic conditions. The base can be potassium hydroxide, sodium hydroxide, or any convenient base. An example of a nucleophilic substitution reaction, which shows a reaction between eugenol and iodoethyl vinyl ether to form an allyl-functionalized vinyl ether monomer (in this embodiment, 4-allyl-2-methoxy-1-(2-(vinyloxy)ethoxy) benzene, "AMB"), is as follows:

Exemplary vinyl ether monomers of the invention include 4-allyl-2-methoxy-1-(2-(vinyloxy)ethoxy)benzene (AMB) (a derivative of eugenol), isoeugenol vinyl ether (see, e.g., Example 11), and cardanolethyl vinyl ether (CEVE; see, e.g., Example 19). The syntheses of some other illustrative functionalized monomers incorporating various plant phenols include the following:

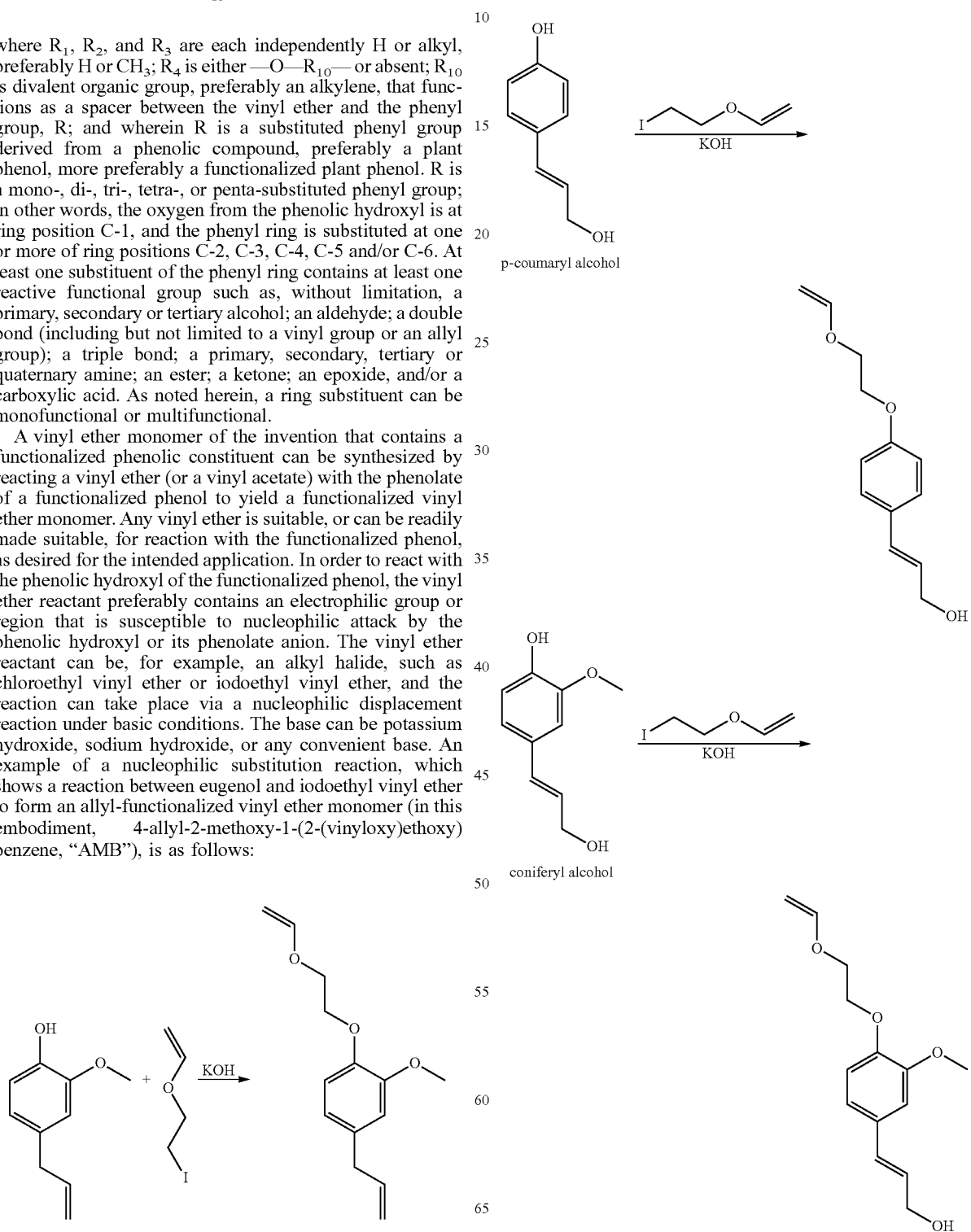

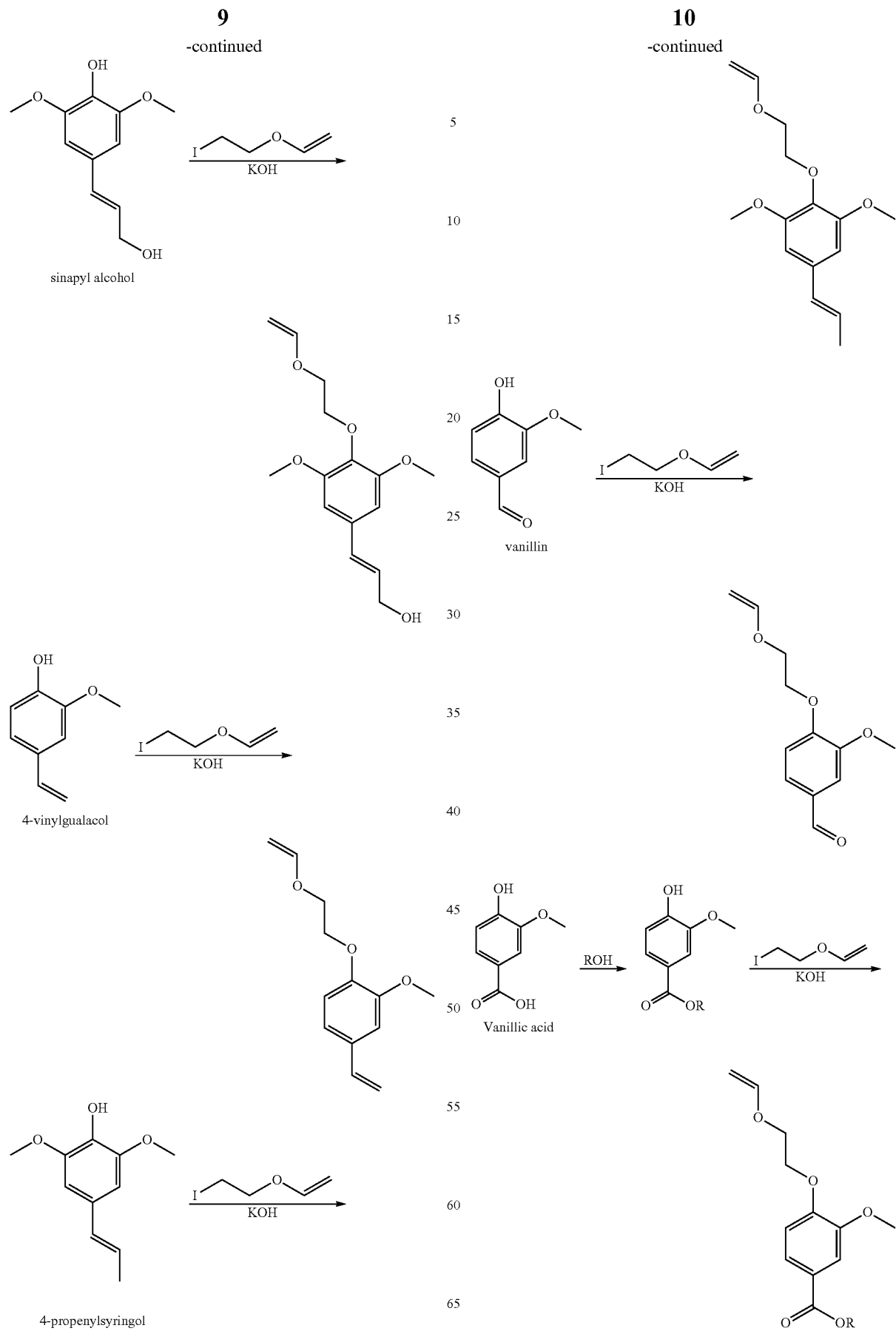

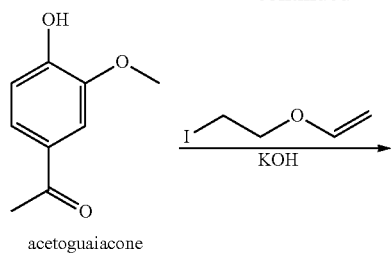
acetoguaiacone

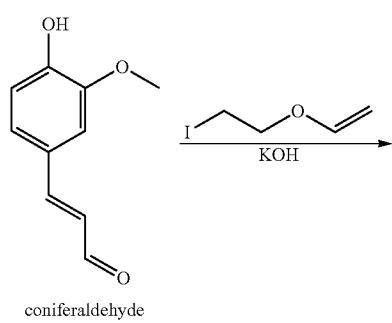
coniferaldehyde

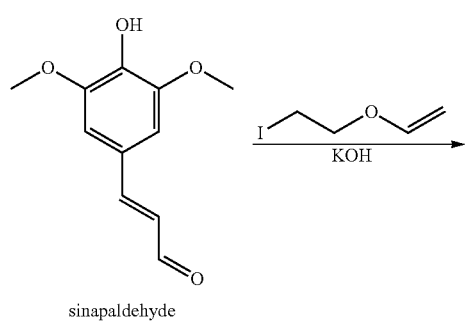
sinapaldehyde

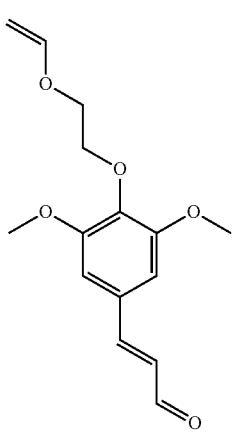

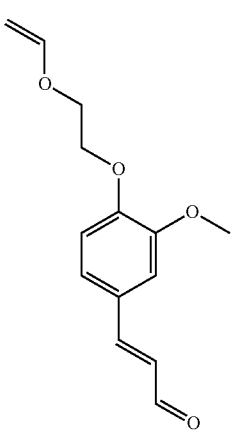

Plant phenols with substituents that have primary alcohols may need to be protected at the primary alcohol prior to the polymerization reaction.

Commonly available hydroxyl-containing vinyl ethers (i.e., hydroxy vinyl ethers), such as, without limitation, an alkylene glycol monovinyl ether exemplified by ethylene glycol monovinyl ether (also known as hydroxyethyl vinyl ether), propylene glycol monovinyl ether (also known as hydroxypropyl vinyl ether), butylene glycol monovinyl ether (also known as hydroxybutyl vinyl ether), tri(ethylene glycol) monovinyl ether (TEGVE), pentaethylene glycol monovinyl ether (PEGVE), can also be utilized as reactants to form the functionalized phenol-containing vinyl ether monomers of the invention, provided the vinyl ether reactant is first modified to derivatize a hydroxyl group (preferably a primary hydroxyl group) so that it contains or becomes a leaving group, thereby making the vinyl ether reactant susceptible to nucleophilic attack by the phenolate anion of the functionalized phenol. For example, the hydroxyl group of a hydroxy vinyl ether reactant, such as hydroxybutyl vinyl ether or hydroxyethyl vinyl ether, can be tosylated, after which the tosylate is displaced by nucleophilic attack of the phenolate anion, for example, of eugenol, vanillin, or cardanol. Any convenient process can be used to convert the functionalized phenol into a vinyl ether monomer; for example, vinylation can be accomplished using acetylene. Other suitable vinyl ethers that can be reacted with the functionalized phenol to yield a functionalized monomer of the invention are well known to the art. Some are described, for example, in Chisholm et al., "Polymers Derived from Plant Oil," US Pat. Pub. 2012-0316309-A1, published Dec. 13, 2012.

When vinyl acetate is reacted with a functionalized phenol, the resulting vinyl ether monomer has the structure R—O—CH=CH$_2$ where R is derived from the phenolic compound. An exemplary synthesis of an ethylenically unsaturated functionalized monomer made using isoeugenol and vinyl acetate reactants is as follows:

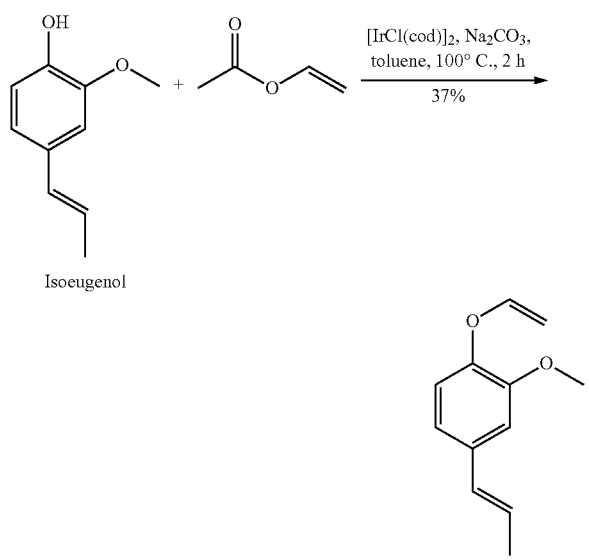

Isoeugenol

If the vinyl acetate is substituted at the vinyl group, the resulting compound will also be substituted at the vinyl ether group. Vinyl acetate or a substituted vinyl acetate can be used as a reactant in order to produce the functionalized vinyl ether monomer of the invention.

Polymers

The invention includes polymers, including homopolymers and copolymers, formed using the functionalized monomers of the invention. Polymers and copolymers include statistical or random copolymers, as well as copolymers with well-defined molecular architectures such as block copolymers, alternating copolymer, star polymers, telechelic polymers, and graft copolymers. A preferred polymer or copolymer is a polyvinyl ether (PVE). In the polymer of the invention, the functionalized pendent phenolic constituent advantageously provides a useful site for derivatization and/or cross-linking.

A polymer or copolymer of the invention contains a monomeric unit derived from the monomers of the invention. The invention encompasses polymers with at least one repeating unit having the following structure:

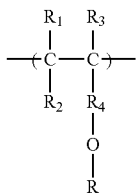

where $R_1$, $R_2$, and $R_3$ are each independently H or alkyl, preferably H or $CH_3$; $R_4$ is either $-O-R_{10}-$ or absent; $R_{10}$ is divalent organic group, preferably an alkylene, that functions as a spacer between the vinyl ether and the phenyl group, R; and wherein R is a substituted phenyl group derived from a phenolic compound, preferably a plant phenol, more preferably a functionalized plant phenol. R is a mono-, di-, tri-, tetra-, or penta-substituted phenyl group; in other words, the oxygen from the phenolic hydroxyl is at ring position C-1, and the phenyl ring is substituted at one or more ring positions C-2, C-3, C-4, C-5 and/or C-6. At least one substituent of the phenyl ring contains at least one reactive functional group such as, without limitation, a primary, secondary or tertiary alcohol; an aldehyde; a double bond (including but not limited to a vinyl group or an allyl group); a triple bond; a primary, secondary, tertiary or quaternary amine; an ester; a ketone; an epoxide, and/or a carboxylic acid. As noted herein, a ring substituent can be monofunctional or multifunctional. A multifunctional ring substituent optionally contains more than one reactive functional group, such as both a double bond and a hydroxyl, or both a double bond and an aldehyde. A multifunctional ring substituent thus allows for the presence of more than one functional group at a single site on the ring. For example, p-coumaryl has a multifunctional ring substituent, namely, a vinyl and a hydroxyl group within the same ring substituent.

Preferably, the polymer or copolymer includes a plurality of monomers, such that for at least one of the plurality of monomers, R is independently a phenyl group derived from a renewable resource such as a plant or plant material.

An exemplary polymer or copolymer, which incorporates a eugenol and/or isoeugenol-derived vinyl ether monomer, has at least one repeating unit having the following structure:

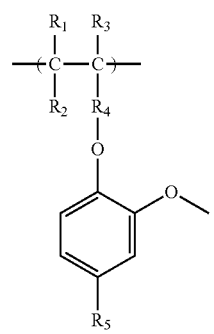

where $R_1$, $R_2$, and $R_3$ are each independently H or alkyl, preferably H or $CH_3$; $R_4$ is $-O-R_{10}-$ or absent; $R_{10}$ is divalent organic group, preferably an alkylene, that functions as a spacer between the vinyl ether and the phenyl group; and $R_5$ is either $CH_2-CH=CH_2$ or $CH=CH-CH_3$ or a mixture of the two. The $R_5$ group, which in this embodiment is derived from eugenol and/or isoeugenol, contains a reactive functionality (in this embodiment, a double bond) that allows the polymer to be derivatized using know chemical derivatization methods such as those illustrated in Example I. Surprisingly, it was found that polymerization processes used to produce the polymers of the invention exclusively consume the vinyl ether double bond. Unsaturated ring substituents other than the vinyl ether group, such as an allyl group or vinyl group, are preserved during the polymerization process. For example, in the case of eugenol and isoeugenol, the allyl group of eugenol constituent or the disubstituted double bond ($-C=C-$) of isoeugenol constituent does not participate in the polymerization reaction, and that polymerization proceeds instead exclusively or almost exclusively through the vinyl ether double bond on the eugenol/isoeugenol-functionalized vinyl ether monomer. This is highly advantageous as it allows the pendant eugenol/isoeugenol group to serve as the site for further derivatization of the polymer or copolymer, for example, by epoxidation as shown herein.

Another exemplary polymer or copolymer, which incorporates a cardanol-derived vinyl ether monomer, has at least one repeating unit having the following structure:

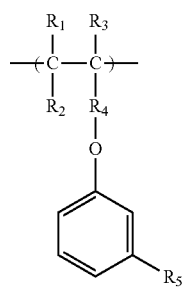

where $R_1$, $R_2$, and $R_3$ are each independently H or alkyl, preferably H or $CH_3$; $R_4$ is —O—$R_{10}$— or absent; $R_{10}$ is divalent organic group, preferably an alkylene, that functions as a spacer between the vinyl ether and the phenyl group; and where $R_5$ is a linear saturated, monounsaturated, or polyunsaturated aliphatic side chain, for example $R_5=C_{15}H_{31-n}$ where n=0, 2, 4, 6. Preferably, the $R_5$ group contains a reactive functionality (in this embodiment, at least one double bond) that allows the polymer to be derivatized using know chemical derivatization methods such as those illustrated in Example XXVI. An exemplary monomer is poly(cardanol ethyl vinyl ether) (polyCEVE), described in Example 20.

In one embodiment, the polymer or copolymer is the product of a carbocationic polymerization reaction in which the polymer molecular weight increases linearly or substantially linearly with monomer conversion, as described in Chisholm et al., "Polymers Derived from Plant Oil," US Pat. Pub. 2012-0316309-A1, published Dec. 13, 2012. In some embodiments, a plot of molecular weight as a function of monomer conversion is approximately linear. One example of this type of carbocationic polymerization reaction is a "living" or controlled carbocationic polymerization. A "living" polymerization is polymerization that occurs substantially without termination or chain transfer reactions resulting in the ability to produce polymers with controlled molecular weight and polymers and potentially copolymers with well-defined molecular architectures such as block copolymers, alternating copolymers, star polymers, telechelic polymers, and graft copolymers. A Lewis base, such as methyl acetate or methyl chloroacetate, is preferably included in the polymerization reaction.

Advantageously, the invention provides a novel functionalized initiator compound that is especially useful in carbocationic polymerization reactions. Example 13 shows synthesis of an allyl-functionalized initiator compound, 1-(2-(4-allyl-2-methoxyphenoxy)ethoxy)ethyl acetate (AMEA). More generally, the initiator compound provided by the invention is a 1-(2-(4-allyl-2-methoxyphenoxy)alkoxy)ethyl acetate. The use of AMEA as an initiator in a polymerization reaction, particularly a carbocationic "living" polymerization involving polymerization of a vinyl ether, produces polymers and copolymers having one or more terminal allyl groups, such as telechelic polymers, which are capable of entering into further polymerization reactions. In a preferred embodiment, the polymerization is terminated with an allyl alcohol such as 2-alloxy ethanol. Subsequent production of block and graft copolymers is facilitated because the block or graft copolymers are formed through utilization of the terminal allyl group on the end-reactive polymer that was derived from the initiator, AMEA. Examples 14 and 15 show exemplary syntheses made possible by the use of the allyl-functionalized initiator AMEA.

The invention also includes a method for making the functionalized initiator compound of the invention, for example by contacting 4-allyl-2-methoxy-1-(2-(vinyloxy)alkoxy)benzene, preferably 4-allyl-2-methoxy-1-(2-(vinyloxy)ethoxy)benzene, with acetic acid under conditions and for a time sufficient to yield the functionalized initiator compound 1-(2-(4-allyl-2-methoxyphenoxy)alkoxy)ethyl acetate, 1-(2-(4-allyl-2-methoxyphenoxy)ethoxy)ethyl acetate (AMEA). Also included in the invention is a method for making a functionalized polymer or copolymer that includes contacting at least one vinyl ether monomer, including but not limited to vinyl ether monomers derived from natural phenols, with the functionalized initiator compound under conditions and for a time sufficient to yield the functionalized polymer or copolymer, wherein the functionalized polymer or copolymer includes a terminal allyl group. The method broadly includes contacting any monomer, such as a vinyl monomer and optionally one or more additional monomers, with the functionalized initiator compound under conditions and for a time sufficient to yield the allyl-functionalized polymer or copolymer. The resultant allyl-functionalized polymer or copolymer can, in turn, be used to form other copolymers. For example, the allyl-functionalized polymer or copolymer can be reacted with at least one second polymer or copolymer, to yield a block or graft copolymer produced through a reaction at the terminal allyl group of the functionalized polymer or copolymer. In a preferred embodiment, the block or graft copolymer includes a poly(dimethylsiloxane) (PDMS).

In another embodiment, the polymer or copolymer is the product of a free radical polymerization. Optionally the resulting copolymer is an alternating copolymer. Optionally, the polymer has a polydispersity index of less than 1.5.

It should be understood that the polymerization reactions described herein can be carried out with, and without, an added initiator compound.

It should be further understood that the invention includes any polymer or copolymer produced by the polymerization reactions described herein.

One example of a useful copolymer is a copolymer containing at least one functionalized vinyl ether monomer as described herein, and at least one polyalkylene glycol monovinyl ether comonomer, such as polyethylene glycol (PEG) ethyl vinyl ether (VEPEG). The resulting copolymer is amphiphilic, further expanding its industrial utility. Other examples of useful copolymers are those containing at least one functionalized vinyl ether monomer as described herein, and tri(ethylene glycol) ethyl vinyl ether; or copolymers formed from copolymerization of at least one functionalized vinyl ether monomer of the invention and at least one styrene monomer. More generally, exemplary copolymers can include repeating units derived from any of the vinyl ether reactants described herein, including without limitation, alkylene glycol alkyl vinyl ethers, exemplified by ethylene glycol ethyl vinyl ether, propylene glycol ethyl vinyl ether, tri(ethylene glycol) ethyl vinyl ether (TEGEVE), tetra(ethylene glycol) ethyl vinyl ether, penta(ethylene glycol) ethyl vinyl ether (PEGEVE), ethylene glycol methyl vinyl ether, propylene glycol methyl vinyl ether, tri(ethylene glycol) methyl vinyl ether (TEGMVE), tetra(ethylene glycol) methyl vinyl ether, penta(ethylene glycol) methyl vinyl ether, cyclohexyl vinyl ether (CHVE), isobutyl vinyl ether, methyl vinyl ether, ethyl vinyl ether, propyl vinyl ether, 2-chloroethyl vinyl ether, octyl vinyl ether, t-butyl vinyl ether, n-butyl vinyl ether, and the like. It should be noted that tri(ethylene glycol) ethyl vinyl ether is sometimes referred to as triethylene glycol ethyl vinyl ether, penta(ethylene glycol)

ethyl vinyl ether is sometimes referred to as pentaethylene glycol ethyl vinyl ether, and so on. Cyclic vinyl ethers, such as 2,3-dihydrofuran and 3,4-dihydro-2H-pyran, are also suitable comonomers for incorporation into the copolymers of the invention. Incorporation of cyclic vinyl ethers into a copolymer is expected to significantly increase the polymer Tg, which is useful for many applications.

Exemplary copolymers derived from eugenol include copolymers of 4-allyl-2-methoxy-1-(2-(vinyloxy)ethoxy) benzene, "AMB") and at least one of penta(ethylene glycol) ethyl vinyl ether (PEGEVE) (see, e.g., Example 8), cyclohexyl vinyl ether (CHVE) (see, e.g., Example 9), 2-(vinyloxy)ethyl soyate (2-VOES) (see, e.g., Example 10), tri (ethylene glycol) ethyl vinyl ether (TEGEVE) (see, e.g., Example 16), tri(ethylene glycol) methyl vinyl ether (TEG-MVE) (see, e.g., Example 17) or maleic anhydride (MA) as a comonomer.

Exemplary copolymers derived from cardanol include copolymers of cardanol ethyl vinyl ether (CEVE) and at least one of cyclohexyl vinyl ether (CHVE) (see, e.g., Example 22) or maleic anhydride (MA) (see, e.g., Example 24) as a comonomer.

In one embodiment of the copolymer of the invention, the comonomer, such as the vinyl ether comonomer, is hydrophilic. Incorporation of a hydrophilic comonomer is useful, for example, in instances where higher water and oxygen transmission rates are desired without sacrificing basic mechanical or physical properties of the polymer backbone. Examples of hydrophilic comonomers include tri(ethylene glycol) ethyl vinyl ether and penta(ethylene glycol) ethyl vinyl ether.

Repeating units derived from other renewable resources can also be used to form a copolymer of the invention. For example, a functionalized vinyl ether monomer of the invention can be copolymerized with plant oil-derived vinyl ethers such as vinyl ethers of soybean oil or corn oil fatty acid esters (VESFA and VECFA, respectively), and/or 2-(vinyloxy)ethyl soyate (2-VOES), as described below and in Chisholm et al., "Polymers Derived from Plant Oil," US Pat. Pub. 2012-0316309-A1, published Dec. 13, 2012.

Comonomers that can be advantageously employed in free-radical polymerization to produce a copolymer of the invention include, without limitation, dimethyl maleate, diethyl maleate, dimethyl fumarate, diethyl fumarate, acrylonitrile, maleimide, N-phenyl maleimide, N-ethyl maleimide, and N-methyl maleimide.

More generally, a copolymer of the invention is formed from at least two different monomers. At least one monomer is a functionalized vinyl ether monomer of the invention as described herein. The additional monomer, or the additional monomers if there is more than one, can be any suitable comonomer. A suitable comonomer can include one or more additional functionalized vinyl ether monomers of the invention, one or more other vinyl ether monomers, or other types of monomers that can be polymerized with the functionalized vinyl ether monomer of the invention. The copolymer of the invention is not limited by the comonomer that can be copolymerized with the vinyl ether monomers of the invention; examples of other comonomers that can be copolymerized with the vinylether monomers described herein can be found in Aoshima et al., Chem Rev 2009, 109, 5245-5287.

More generally, any comonomer that imparts the desired properties to the resulting copolymer can be incorporated into the copolymer of the invention.

Copolymerization reactions can be using any suitable copolymerization technique. For example, carbocationic polymerization can be used, as described in Chisholm et al., "Polymers Derived from Plant Oil," US Pat. Pub. 2012-0316309-A1, published Dec. 13, 2012. Another example of a polymerization reaction method that can be used is free radical polymerization. For example, the vinyl ether monomers of the invention can be copolymerized with other vinyl monomers that are electron deficient, that is, which possess strongly electron withdrawing groups, such as an anhydride, e.g. maleic anyhydride, or a nitrile, such as acrylonitrile, or fluoro, such as chlorotrifluoroethylene, using free radical polymerization. Monomers with strongly electron withdrawing groups are known to the art and further exemplified in D. Braun and F. Hu, "Polymers from non-homopolymerizable monomers by free radical processes," Prog. Polymer Sci. (2006) 31, 239-276.

See, e.g., Chisholm et al., "Polymers Derived from Plant Oil," US Pat. Pub. 2012-0316309-A1, published Dec. 13, 2012, for exemplary methods of synthesis of the copolymers of the invention. The invention is not, however, intended to be limited by the method of polymerization or copolymerization used to form the polymer or copolymer.

The molecular weight distribution (MWD, also known as the polydispersity index, PDI) for the polymer of the invention is typically less than 2 and can be less than 1.8, less than 1.5, and is preferably less than 1.4. Thus, in one embodiment, the polymer of the invention has a PDI of less than 2.0, less than 1.9, less than 1.8, less than 1.7, less than 1.6, less than 1.5, less than 1.4, less than 1.3, less than 1.2, or less than 1.1. In another embodiment, the polymer of the invention has a PDI of between 1.1 and 1.6, more preferably between 1.2 and 1.4.

The polymers and or copolymers of the invention can be cross-linked or non-crosslinked. Advantageously, the reactive functional groups on the phenolic constituent can be employed to cross-link the polymer to produce, for example, useful thermoset networks.

Derivatization of the Pendant Phenolic Constituent

The monomer or polymer of the invention can be derivatized or activated by reacting the reactive functional group on the phenolic constituent with a selected reactant to achieve a desired property. Typically, derivatization or activation of the reactive functional group is performed subsequent to polymerization, but it may be performed prior to or during polymerization. The invention includes polymers (and monomers) that have been activated by epoxidation, as well as acrylate-functional and polyol functional polymers synthesized using, for example, an epoxy-functional intermediate. Thus, the monomer or polymer can be chemically treated, altered or derivatized for further use according to the desired application, for example by epoxidation, acrylation, and other chemical reactions to produce epoxidized derivatives, acrylates, polyols and the like. Treatment may or may not involve polymer cross-linking.

Exemplary derivatizations of polymers derived from eugenol, wherein the reactive functional group present on the phenolic constituent is an allyl group, are shown below:

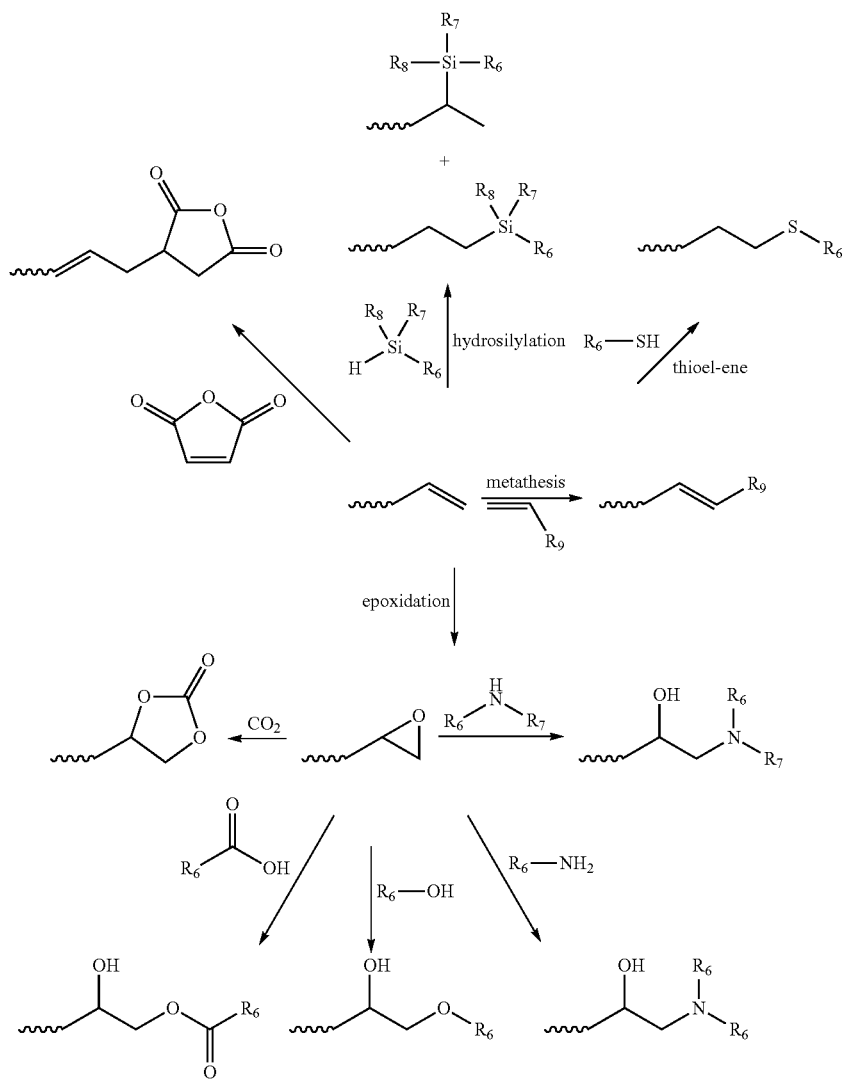

These exemplary derivatizations include epoxidation, hydrosilylation, maleation through the ene reaction, sulfide formation through the thiol-ene reaction, amination through epoxide ring-opening with an amine, etherification through epoxide ring-opening reactions with an alcohol, hydroxylation through epoxide hydrolysis, metathesis, and so on. In some embodiments, monomers may be derivatized prior to polymerization. However, derivatization after polymerization is preferred because some of the functionalities added by derivatization, such as epoxide or hydroxyl, can react or interfere with the polymerization process.

Epoxidized polymers or copolymers (also referred to as epoxy-functional or epoxide-functional) are well-suited for use to produce curable coating compositions. The epoxidized coating composition can be cured using radiation e.g., UV-curing (e.g., via cationic photopolymerization), using an amine curing agent, using an anhydride-functional curing agent and optionally a tertiary amine catalyst, acid catalyst, or any suitable curing agent or method. Surface coatings, composites, adhesives, and plastics can thus be readily generated from the epoxidized polymer or further derivatives thereof.

An activated epoxide intermediate can be further derivatized, for example, by reaction with a primary or secondary amine or alcohol, a carboxylic acid, aldehyde, carbon dioxide, and so on. For example, incorporation of acrylate groups or alcohol groups typically first involves the generation of an epoxide intermediate. The double bonds can be derivatized using epoxidation, Diels-Alder chemistry, metathesis, or thiol-ene chemistry. Derivatives such as epoxy-functional, acrylate-functional and alcohol-functional (polyol) polymers are likewise included in the invention.

In another embodiment, the invention provides an acrylate-functional polymer or copolymer. For example, an epoxidized polymer or copolymer of the invention can be reacted with acrylic acid to yield an acrylate-functional polymer. The acrylated polymer can be cured, for example using radiation (e.g., UV), and a free-radical photoinitiator, such as 2,2-dimethoxy-2-phenylacetophenone, heat and a free-radical thermal initiator, such as a peroxide or azo compound, or heat and a di- or multi-functional amine (Michael addition).

In yet another embodiment, the invention provides a polyol polymer or copolymer. For example, an epoxidized polymer or copolymer of the invention can be subjected to a ring-opening reaction to produce a polyol, which finds use in the preparation of, for example, polyurethanes, alkyd resins, and the like.

In yet another embodiment, the invention provides a silicon-containing polymer or copolymer. A polymer or copolymer of the invention can be silylated via hydrosilylation at a double bond on the pendant phenolic constituent, for example. Silylation can be complete, or partial. If partial, non-silylated double bonds are available for further derivatization or crosslinking. For example, an incompletely silylated polymer or copolymer of the invention can be blended with siloxane and cured with a hydride-functional siloxane, yielding a modified, cross-linked hybrid siloxane coating. Silylated coatings have many uses, such as in marine applications as anti-fouling agents, or in medical applications.

The utility of these compositions largely stems from the wide variety of pendent functional groups that can be incorporated into the polymer to enable a variety of applications including coatings, composites, and plastics. In addition, the polymers of the invention can have a high renewable content, since plant phenolics, such as eugenol, iso-eugenol, vanillin, and cardanol, can be used to produce the polymers.

Plant oil-based materials are currently commercially available for a large number on non-food applications, such as lubricants, hydraulic fluids, coatings, drying agents, plastics, composites, insulators, soaps, candles, cosmetics, etc. Essentially, and importantly, the phenolic-derived polymers of the invention, such as polymers derived from eugenol, isoeugenol, vanillin, and cardanol, can be used for any application which currently utilizes a renewable polymer, such as a polymer derived from soybean oil. Due to the renewable aspect of plant derivatives, many industries are trying to use more chemicals from renewable sources. The polymers of the invention can be used in any and all of these applications. Also included are liquids and solids, including articles of manufacture of any type, that contain monomers or polymers as described herein, including lubricating and hydraulic fluids, gels, plastics, composites, elastomers, polyurethanes, additives, adhesives and the like.

As used herein, the terms "aliphatic" or "aliphatic group" mean a saturated or unsaturated linear (i.e., straight chain), cyclic, or branched hydrocarbon group. The hydrocarbon or hydrocarbon group can be substituted or unsubstituted. The term "aliphatic" encompasses monovalent and divalent aliphatic groups, including alkyl (e.g., —CH$_3$) (or alkylene if within a chain such as —CH$_2$—), alkenyl (or alkenylene if within a chain), and alkynyl (or alkynylene if within a chain) groups, as well as substituted forms thereof, for example.

The terms "alkyl" or "alkyl group" mean a saturated linear or branched hydrocarbon group including, for example, methyl, ethyl, isopropyl, t-butyl, amyl, heptyl, dodecyl, octadecyl, amyl, 2-ethylhexyl, and the like, as well as their divalent counterparts. "Alkyl" and "alkylene" are also meant to include substituted alkyls and alkylenes. Suitable substituents include aryl groups (which may themselves be substituted), as in the case where the "alkyl" is a phenyl-substituted methyl group (e.g., a benzyl moiety). Other suitable substituents include heterocyclic rings (saturated or unsaturated and optionally substituted), hydroxy groups, alkoxy groups (which is meant to include aryloxy groups (e.g., phenoxy groups)), thiol groups, alkylthio groups, arylthio groups, amine groups (which is meant to include unsubstituted, monosubstituted, or disubstituted (e.g., with aryl or alkyl groups) amine groups), carboxylic acid groups (which is meant to include COOH groups as well as carboxylic acid derivatives, e.g., carboxylic acid esters, amides, etc.), phosphine groups, sulfonic acid groups, halogen atoms (e.g., F, Cl, Br, and I), and the like. Further, alkyl groups bearing one or more alkenyl or alkynyl substituents (e.g., a methyl group itself substituted with a prop-1-en-1-yl group to produce a but-2-en-1-yl substituent or a methyl group itself substituted with a vinyl group to produce an allyl substituent) are meant to be included in the meaning of "alkyl."

The terms "alkenyl" or "alkenyl group: mean an unsaturated, linear or branched monovalent or divalent hydrocarbon group with one or more olefinically unsaturated groups (i.e., carbon-carbon double bonds), such as a vinyl group. Alkenyl groups include, for example, ethenyl, propenyl, butenyl, 1-methyl-2-buten-1-yl, and the like.

The term "alkynyl group" means an unsaturated, linear or branched monovalent or divalent hydrocarbon group with one or more carbon-carbon triple bonds. Representative alkynyl groups include, but are not limited to, ethynyl, 2-propynyl (propargyl), 1-propynyl, and the like.

The term "aliphatic" also encompasses monovalent or divalent cyclic hydrocarbons such as cycloaliphatic groups or heterocyclic groups. The term "cycloaliphatic" refers to a cyclic or polycyclic hydrocarbon group, which may have properties resembling those of linear aliphatic groups. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. The term "cycloaliphatic" also includes aliphatic rings that are fused to one or more aromatic or nonaromatic rings, such as decahydronaphthyl or tetrahydronaphthyl, where the radical or point of attachment is on the aliphatic ring. The term "heterocyclic group" means a cyclic or polycyclic closed ring hydrocarbon in which one or more of the atoms in the ring is an element other than carbon (e.g., nitrogen, oxygen, sulfur, etc.).

Unless otherwise specified, an aliphatic group can contain 1 or 2 or 3 or 4, and so on, up to 38 or 39 or 40 carbon atoms; that is, 1 to 40 carbon atoms. In certain embodiments, aliphatic groups contain 1 to 20 carbon atoms. In certain embodiments, aliphatic groups contain 2 to 20 carbon atoms. In certain embodiments, aliphatic groups contain 1 to 12 carbon atoms, or 1 to 8 carbon atoms, or 1 to 6 carbon atoms, 1 to 5 carbon atoms, 1 to 4 carbon atoms, 1 to 3 carbon atoms, or 1 to 2 carbons atoms. Exemplary aliphatic groups include, but are not limited to, linear or branched alkyl, alkylene, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

An aliphatic group may be unsubstituted, or optionally substituted with one or more substituents. "Substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents include, but are not limited to, alkyl, alkenyl, alkynyl, cycloalkyl, heterocycloalkyl, aryl, heteroaryl, aroyl, halo (e.g., F, Cl, Br and I), hydroxy, oxo, nitro, alkoxy, amino, amido, imino, azido, mercapto, acyl, carbamoyl, carboxy, carboxamido, amidino, guanidino, thiol, alkylthio, arylthio, sulfonyl, sulfinyl, sulfonamido, phosphine, formyl, cyano, and ureido groups.

The term "alkoxy", as used herein refers to an alkyl group, as previously defined, attached to the parent molecule through an oxygen atom. Examples of alkoxy, include but are not limited to, methoxy, ethoxy, propoxy, isopropoxy, n-butoxy, tert-butoxy, neopentoxy, and n-hexoxy.

The term "acyl", as used herein, refers to a carbonyl-containing functionality, e.g., —C(=O)R', wherein R' is hydrogen or an optionally substituted aliphatic, heteroaliphatic, heterocyclic, aryl, heteroaryl group, or is a substituted (e.g., with hydrogen or aliphatic, heteroaliphatic, aryl, or heteroaryl moieties) oxygen or nitrogen containing functionality (e.g., forming a carboxylic acid, ester, or amide functionality). The term "acyloxy", as used here, refers to an acyl group attached to the parent molecule through an oxygen atom.

The terms "aromatic," "aromatic group," "aryl" and "aryl group" mean a mono- or polynuclear aromatic hydrocarbon group. These hydrocarbon groups may be substituted with heteroatoms, which can be in the form of functional groups. The term "aromatic" or "aryl" used alone or as part of a larger moiety as in "aromatic hydrocarbon," "aralkyl," "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring" or "aromatic ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

In describing substituents, the term "radical" is sometimes used. In this context, "radical" means a moiety or functional group having an available position for attachment to the structure on which the substituent is bound. In general the point of attachment would bear a hydrogen atom if the substituent were an independent neutral molecule rather than a substituent.

The term "heteroatom" means an element other than carbon (e.g., nitrogen, oxygen, sulfur, chlorine, etc.). A "hetero-" moiety as described herein, such as a heteroaliphatic group, a heterocyclic group and the like, refers to a moiety having, in place of one or more carbon atoms, a heteroatom independently selected from nitrogen, oxygen, or sulfur. Examples of saturated or partially unsaturated heterocyclic groups include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unless otherwise specified, "a," "an," "the," and "at least one" are used interchangeably and mean one or more than one.

EXAMPLES

The present invention is illustrated by the following examples. It is to be understood that the particular examples, materials, amounts, and procedures are to be interpreted broadly in accordance with the scope and spirit of the invention as set forth herein.

Example 1

Synthesis of 4-allyl-2-methoxy-1-(2-(vinyloxy)ethoxy)benzene (AMB) using 2-iodoethyl vinyl ether 4-allyl-2-methoxy-1-(2-(vinyloxy)ethoxy)benzene (AMB) was synthesized as illustrated in FIG. 1.

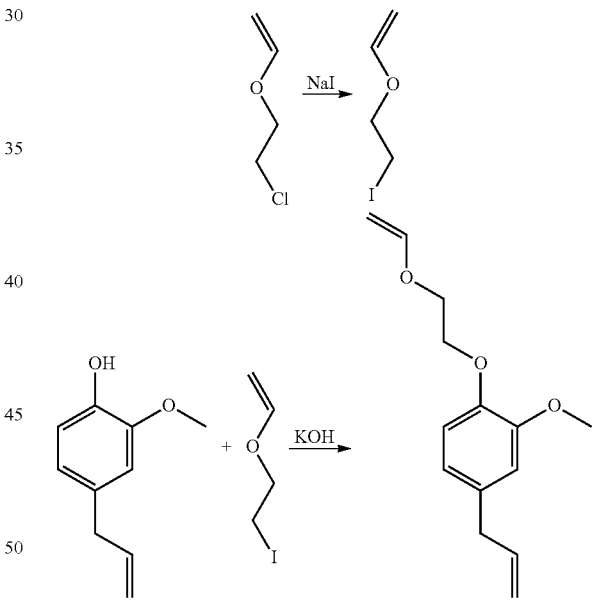

A detailed description of the synthesis is as follows: 100.65 g of 2-chloroethyl vinyl ether (TCI Chemicals, >97%), 200.16 g of sodium iodide (Alfa Aesar, 99+%), and 730 g of dry acetone were combined in a 2-liter, 3-neck, round-bottom flask and heated at a temperature of 60° C. for 24 hours. Next, the reaction mixture was cooled to room temperature and diluted with 600 ml of diethyl ether. The organic layer was washed thrice with deionized water and dried with anhydrous magnesium sulfate. The colorless product was recovered by vacuum stripping of the diethyl ether and 2-chloroethyl vinyl ether at a temperature of 40° C. and a pressure of 50 mmHg. Proton nuclear magnetic resonance spectroscopy (H$^1$ NMR) was used to confirm the production of 2-iodoethyl vinyl ether. The product was a mixture of 2-iodoethyl vinyl ether and 2-chloroethyl vinyl ether containing 90 mole percentage of 2-iodoethyl vinyl ether. $^1$H NMR (CDCl$_3$) δ 6.44 ppm (q, 1H, OC$\underline{H}$=C), 4.19, 4.05 ppm (dd, 2H, C$\underline{H}$=C), 3.95 ppm (t, 2H, OC$\underline{H}_2$), 3.3 ppm (t, 2H, C$\underline{H}_2$I).

20 g of the 90% pure 2-iodoethyl vinyl ether obtained according to the procedure described above was combined with 100 ml of N,N-dimethylformamide (VWR, 99.8%), 22.4 g of eugenol (Sigma-Aldrich, 99%), and 9 g of potassium hydroxide (Sigma-Aldrich, reagent grade, 90%, flakes) in a 1000 ml round-bottom flask equipped with a reflux condenser. The solution produced was stirred at room temperature for 19 hours. After this period, 75 ml of methylene chloride was added to the vessel. Next, the solution was transferred to a separatory funnel and washed three times with 40 ml of 2N potassium hydroxide in deionized (DI) water to remove excess eugenol. After washing with potassium hydroxide, the organic layer was washed multiple times with DI water until the aqueous layer was neutral pH as indicated by litmus paper. Finally, the organic layer was dried with anhydrous magnesium sulfate and the product isolated by vacuum stripping volatiles at 30° C. and a pressure of 5 millibar for 12 hours. $^1$HNMR was used to confirm the production of AMB: $^1$H NMR (CDCl$_3$) δ 6.5 ppm (q, 1H, OC$\underline{H}$=C), 4.22 ppm-4.25 ppm (m, 2H, C$\underline{H}_2$=C—O), 4.0 ppm-4.2 ppm (m, 4H, C$\underline{H}_2$—CH$_2$), 3.3 ppm (d, 2H, C=C—C$\underline{H}_2$), 5.9 ppm (m, 1H, C=C$\underline{H}$—C), 5.1 (m, 2H, C$\underline{H}_2$=C—C), 3.8 ppm (s, 3H, C$\underline{H}_3$), 6.7 ppm, 6.9 ppm (m, 3H, Ar—$\underline{H}$).

AMB was also produced using a different process in which 100 ml of methanol was used in place of N,N-dimethylformamide and the reaction time and temperature increased to 48 hours and 60° C., respectively. As indicated by $^1$H NMR, this process also yielded the desired product, AMB, but the color of the product was lighter than that obtained using DMF as the reaction solvent.

Example 2

Synthesis of 4-allyl-2-methoxy-1-(2-(vinyloxy) ethoxy)benzene using 2-chloroethyl vinyl ether Example 1 involved the conversion of 2-chloroethyl vinyl ether to 2-iodoethyl vinyl ether during the synthesis of AMB. This example demonstrates that AMB can be produced directly from 2-chloroethyl vinyl ether. 7 g of 2-chloroethyl vinyl ether, 16.18 g of eugenol, 5.23 g of potassium hydroxide, and 35 ml of N,N-dimethylformamide were combined in a 250 ml, 2-neck, round-bottom flask and heated at a temperature of 80° C. for 24 hours. Next, the reaction mixture was cooled to room temperature and diluted with 30 ml of methylene chloride. The methylene chloride was washed three times with 30 ml of 2N potassium hydroxide solution in DI water to remove the excess eugenol. Next, the organic layer was washed multiple times with DI water until the aqueous layer was at neutral pH as indicated with litmus paper and then dried with anhydrous magnesium sulfate. The product was isolated by after evaporation of volatiles at a temperature of 30° C. and a pressure of 5 millibar for 12 hours. Successful production of AMB was determined using $^1$H NMR.

Example 3

Synthesis and Characterization of Poly[4-allyl-2-methoxy-1-(2-(vinyloxy)ethoxy)benzene] (polyAMB)

Poly[4-allyl-2-methoxy-1-(2-(vinyloxy)ethoxy)benzene] (polyAMB) was synthesized as follows: Toluene and methyl acetate (MAc, Sigma-Aldrich, >99%) were distilled over calcium hydride just prior use. AMB was dried with anhydrous magnesium sulfate just before use. 1-isobutoxyethyl acetate (IBEA) was synthesized and dried according to the procedure described by Aoshima and Higashimura [Aoshima, S.; Higashimura, T., "Living cationic polymerization of vinyl monomers by organoaluminum halides. 3. Living polymerization of isobutyl vinyl ether by ethyldichloroaluminum in the presence of ester additives." *Macromolecules* 1989, 22 (3), 1009-13]. Ethyl aluminum sesquichloride (97%, Sigma-Aldrich) was diluted with dry toluene to produce a 25 weight percent solution. 100 g of AMB, 68.3 mg of IBEA, 15.82 g of MAc and 525 g of dry toluene were combined in a dry 1000 ml, 2-liter, round-bottom flask fitted with an overhead stirrer. The reaction mixture was cooled to 0° C. by submerging the reaction vessel into a heptane bath inside a dry box. The polymerization was initiated by the addition of 5.28 g of the ethylaluminum sesquichloride solution (25 wt. % in toluene). The reaction was terminated after 8 hours by the addition of 1000 ml of chilled methanol which caused the polymer to precipitate. The polymer was isolated and washed multiple times with methanol. The purified polymer was dried under vacuum overnight at a temperature of 30° C.

Polymer molecular weight was characterized using a high-throughput Symyx Rapid Gel Permeation Chromatography equipped with an evaporative light scattering detector (PL-ELS 1000) and polystyrene standards. The number-average molecular weight and molecular weight distribution of the polyAMB expressed relative to polystyrene standards was 13,680 g/mole and 1.34, respectively. The thermal properties of the polymer were determined using differential scanning calorimetry (Q1000 from TA Instruments) by first heating the sample from 30° C. to 50° C. at a heating rate of 10° C./minute (1$^{st}$ heat), cooling from 50° C. to −120° C. at a cooling rate of 10° C./minute (cooling), and reheating from −120° C. to 120° C. at a heating rate 10° C./minute (2$^{nd}$ heat). The thermogram obtained from the 2$^{nd}$ heat showed a glass transition at 3.3° C.

Example 4

Further Characterization of PolyAMB Polymerization

Polymerization kinetics were determined by carrying out multiple polymerizations inside a glove box at 0° C. using a series of dry 40 ml vials. Toluene, MAc, and methyl chloroacetate, MCAc (Sigma-Aldrich, 99%) were distilled over calcium hydride before use. In each vial, toluene, IBEA, AMB, and either MAc or MCAc were combined and the solution cooled to 0° C. Each polymerization was initiated by the addition of a 25 weight percent solution of ethyl aluminum sesquichloride solution in toluene. Table I lists the chemical composition of each polymerization. Aliquots of known weight were withdrawn at predetermined time intervals and terminated by the addition of 5 ml of methanol, which caused the polymer to precipitate. The polymer was isolated and washed with methanol using centrifugation. Prior to measuring polymer yield, all volatiles were removed under vacuum.

TABLE I

Chemical composition of AMB polymerizations used to determine polymerization kinetics.

| Polymerization Identification | Wt. of AMB (g) | Wt. of IBEA (mg) | Wt. of MAc (mg) | Wt. of MCAc (g) | Wt. of toluene (g) | Wt. of $Et_{1.5}AlCl_{1.5}$ solution (µl) |
|---|---|---|---|---|---|---|
| PolyAMB/1IBEA/100MAc  | 2 | 6.8 | 316 | 0    | 10.5 | 117 |
| PolyAMB/1IBEA/250MAc  | 2 | 6.8 | 791 | 0    | 10.5 | 117 |
| PolyAMB/0IBEA/250MAc  | 2 | 0   | 791 | 0    | 10.5 | 117 |
| PolyAMB/1IBEA/250MCAc | 2 | 6.8 | 0   | 1.16 | 10.5 | 117 |

$[M]_o$ and $[M]_t$ represent the initial concentration and the concentration at time (t) of the monomer (i.e. AMB) where $[M]_t$ was calculated from weight of polyAMB produced at time t. For each polymerization, a plot of $\ln([M]_o/[M]_t)$ as a function of polymerization time yielded a straight line that passed through the origin. The slope and correlation coefficient for each plot generated from each polymerization are listed in Tables II-V. From the slope of each straight line, the polymerization rate constant was calculated.

TABLE II

Data used to generate the plot of $\ln\{[M]_o/[M]_t\}$ as a function of polymerization time for PolyAMB/1IBEA/100MAc.

| Polymerization time (min) | $\ln\{[M]_o/[M]_t\}$ | Slope | Correlation coefficient |
|---|---|---|---|
| 0     | 0    | 0.07 | 0.92 |
| 1.75  | 0.31 |      |      |
| 3.9   | 0.48 |      |      |
| 7.83  | 0.68 |      |      |
| 15.47 | 1.11 |      |      |
| 23.0  | 1.48 |      |      |

TABLE III

Data used to generate the plot of $\ln\{[M]_o/[M]_t\}$ as a function of polymerization time for PolyAMB/1IBEA/250MAc.

| Polymerization time (min) | $\ln\{[M]_o/[M]_t\}$ | Slope | Correlation coefficient |
|---|---|---|---|
| 0   | 0    | 0.046 | 0.98 |
| 12  | 0.31 |       |      |
| 19  | 0.44 |       |      |
| 37  | 0.70 |       |      |
| 76  | 1.19 |       |      |
| 108 | 1.53 |       |      |
| 142 | 1.90 |       |      |
| 203 | 2.23 |       |      |

TABLE IV

Data used to generate the plot of $\ln\{[M]_o/[M]_t\}$ as a function of polymerization time for PolyAMB/0IBEA/250MAc.

| Polymerization time (min) | $\ln\{[M]_o/[M]_t\}$ | Slope | Correlation coefficient |
|---|---|---|---|
| 0   | 0        | 0.013 | 0.96 |
| 10  | 0.270978 |       |      |
| 19  | 0.344708 |       |      |
| 36  | 0.579753 |       |      |
| 76  | 1.078878 |       |      |
| 108 | 1.430755 |       |      |
| 142 | 1.602589 |       |      |

TABLE V

Data used to generate the plot of $\ln\{[M]_o/[M]_t\}$ as a function of polymerization time for PolyAMB/1IBEA/250MCAc.

| Polymerization time (min) | $\ln\{[M]_o/[M]_t\}$ | Slope | Correlation coefficient |
|---|---|---|---|
| 0    | 0    | — | — |
| 2.25 | 2.25 |   |   |
| 2.35 | 2.35 |   |   |
| 2.45 | 2.45 |   |   |
| 2.34 | 2.34 |   |   |

Polymer molecular weight and molecular weight distribution was characterized using a high-throughput Symyx Rapid Gel Permeation Chromatography equipped with an evaporative light scattering detector (PL-ELS 1000) and polystyrene standards. Tables VI to IX list the percent monomer conversion, number-average molecular weight relative to polystyrene standards, and molecular weight distribution data as a function of polymerization time for each of the four polymerizations. As illustrated in Table IX, the polymerization from PolyAMB/1IBEA/250MCAc was too fast to adequately generate a plot.

TABLE VI

Data used to generate a plot of number-average molecular weight (expressed relative to polymer styrene standards) as a function of percentage of monomer conversion for PolyAMB/1IBEA/100MAc.

| Reaction time (min) | % Monomer Conversion | GPC number Average Molecular Weight | PDI | Slope | Y-axis intercept | Correlation coefficient |
|---|---|---|---|---|---|---|
| 1.75  | 26.92 | 10440 | 1.33 | 38.1 | 9344 | 0.98 |
| 3.88  | 38.36 | 10840 | 1.33 |      |      |      |
| 7.83  | 49.43 | 11090 | 1.37 |      |      |      |
| 15.47 | 67.03 | 11970 | 1.34 |      |      |      |
| 23    | 77.32 | 12130 | 1.36 |      |      |      |
| 54.45 | 88.63 | 12860 | 1.34 |      |      |      |

TABLE VII

Data used to generate a plot of number-average molecular weight (expressed relative to polymer styrene standards) as a function of percentage of monomer conversion for PolyAMB/1IBEA/250MAc.

| Reaction time (min) | % Monomer Conversion | GPC number Average Molecular Weight | PDI | Slope | Y-axis intercept | Correlation coefficient |
|---|---|---|---|---|---|---|
| 12 | 26.71 | 8614 | 1.25 | 52.4 | 7047 | 0.98 |
| 19 | 35.63 | 8697 | 1.3 | | | |
| 37 | 50.40 | 9613 | 1.29 | | | |
| 76 | 69.45 | 10920 | 1.28 | | | |
| 108 | 78.42 | 11180 | 1.28 | | | |
| 142 | 85.02 | 11380 | 1.29 | | | |

TABLE VIII

Data used to generate a plot of number-average molecular weight (expressed relative to polymer styrene standards) as a function of percentage of monomer conversion for PolyAMB/0IBEA/250MAc.

| Reaction time (min) | % Monomer Conversion | GPC number Average Molecular Weight | PDI | Slope | Y-axis intercept | Correlation coefficient |
|---|---|---|---|---|---|---|
| 10 | 23.74 | 11050 | 1.21 | 132.8 | 7867 | 0.99 |
| 19 | 29.16 | 11650 | 1.25 | | | |
| 36 | 44 | 13760 | 1.29 | | | |
| 76 | 66 | 16790 | 1.28 | | | |
| 108 | 76.1 | 17680 | 1.33 | | | |
| 142 | 79.86 | 18620 | 1.33 | | | |

TABLE IX

Data used to generate a plot of number-average molecular weight (expressed relative to polymer styrene standards) as a function of percentage of monomer conversion for PolyAMB/1IBEA/250MAc.

| Reaction time (min) | % Monomer Conversion | GPC number Average Molecular Weight | PDI | Slope | Y-axis intercept | Correlation coefficient |
|---|---|---|---|---|---|---|
| 2 | 89.49 | 11370 | 1.41 | — | — | — |
| 3.05 | 90.43 | 11180 | 1.4 | | | |
| 3.92 | 91.33 | 11050 | 1.43 | | | |
| 4.72 | 90.34 | 11520 | 1.39 | | | |
| 6.03 | 89.57 | 11120 | 1.41 | | | |
| 7.12 | 87.8 | 11310 | 1.4 | | | |

Example 5

Coatings from PolyAMB Produced Using Oxidative Cure

An example of the production of a cured film of polyAMB produced using an oxidative cure mechanism is as follows: A catalyst mixture for oxidative cure was produced by mixing 26.6 mg of cobalt 2-ethylhexanoate (OMG Americas, 12% cobalt), 263 mg of zirconium 2-ethylhexanoate (OMG Americas, 18% zirconium), and 1.6 g of zinc carboxylate (Dura Chemicals, 8% in mineral spirits) in a 40 ml vial using a vortex mixture. 9 g of a 73 weight percent solution of polyAMB in tetrahydrofuran (THF) and 540 mg of the catalyst mixture were mixed with a FlackTek mixer using 3500 rpm for 3 minutes. The solution was coated over seven steel Q-panels, one Teflon® coated glass panel, and one glass panel. The wet film thickness was approximately 0.2 mm and the films cured in an oven at 140° C. for 2 hours.

The cured coating was characterized by MEK double rubs (ASTM D 5402-93), pencil hardness (ASTM D 3363-00), Konig pendulum hardness (ASTM D 4366-95), mandrel bend test (ASTM D 522-93a), and crosshatch adhesion test (ASTM D 3359-97). Free film specimens were characterized using dynamic mechanical analysis (Q800 from TA Instruments). The experiment was carried out from −40° C. to 120° C. using a heating rate of 5° C./min., frequency of 1 Hz, and strain amplitude of 0.02%. The glass transition temperature ($T_g$) was obtained from the peak maximum in the tan δ response. The thermal properties were determined using differential scanning calorimetry (Q1000 from TA Instruments) by first heating the sample from 30° C. to 120° C. at a heating rate of 10° C./minute ($1^{st}$ heat), cooling from 120° C. to −120° C. at a cooling rate of 10° C./minute (cooling), and reheating from −120° C. to 120° C. at a heating rate 10° C./minute ($2^{nd}$ heat). The $T_g$ was reported from the thermogram obtained from the $2^{nd}$ heat. Tensile testing of dumb bell-shaped specimens (ASTM D 638-5) stamped from free films was carried out using an Instron tensile tester fitted with a 100 N load cell. The displacement rate of the movable clamp was set as 1 mm/minute. Data reported was the average of 5 replicate measurements. Table X list the data obtained for the cured coating.

TABLE X

Data obtained for cured coatings from
polyAMB produced using oxidative cure.

| Measurement | Value Obtained |
|---|---|
| ASTM Testing of Coated Substrates | |
| Average thickness (μm) | 72 ± 6 |
| König pendulum hardness (glass substrate), sec. | 14 |
| König pendulum hardness (steel substrate), sec. | 15 |
| Pencil hardness | HB |
| Cross hatch adhesion (steel substrate) | 5B |
| Conical mandrel bend test, Elongation % | 100 |
| Reverse impact (in-lb) | >172 |
| MEK double rubs | 72 ± 17 |
| Tensile Testing of Free Film Specimens | |
| Young's modulus (MPa) | 10.4 ± 3.6 |
| Toughness (mJ) | 8.1 ± 2.2 |
| Elongation at Break (%) | 64 ± 4 |
| Dynamic Mechanical Analysis of Free Films | |
| Storage modulus at 90° C. (MPa) | 2.26 |
| Tg from tanδ (° C.) | 21 |
| Differential Scanning Calorimetry | |
| Tg (° C.) | 12 |

Example 6

Synthesis and Characterization of an
Epoxy-Functional PolyAMB

PolyAMB was epoxidized as follows: 30 g of polyAMB, 600 ml of methylene chloride, and 57.42 g of 3-chloroperbenzoic acid (Sigma-Aldrich, <77%) were combined in a 1000 ml, 2-liter, round bottom flask and stirred continuously at a temperature of 22° C. After 24 hours of reaction, the epoxidized polymer was isolated by precipitation into methanol and drying overnight under vacuum. The thermal properties of the polymer were determined using differential scanning calorimetry (Q1000 from TA Instruments) by first heating the sample from 30° C. to 50° C. at a heating rate of 10° C./minute ($1^{st}$ heat), cooling from 50° C. to −120° C. at a cooling rate of 10° C./minute (cooling), and reheating from −120° C. to 120° C. at a heating rate 10° C./minute ($2^{nd}$ heat). The thermogram obtained from the $2^{nd}$ heat showed a glass transition at 27.5° C.

Example 7

Cured Coating Produced from Epoxidized
PolyAMB and an Anhydride Curing Agent 10 g of epoxidized polyAMB (E-polyAMB) with an epoxy equivalent weight of 445 g/mole, 2.22 g of 2-butanone, and 1.04 g of hexahydro-4-methylphthalic anhydride (HMPA, Sigma-Aldrich, 96%) were mixed with a FlackTek mixer using 3500 rpm for 2 minutes. The solution was coated over six steel Q-panels, one Teflon® coated glass panel, and one glass panel. The wet film thickness was approximately 0.2 mm and the film cured in a forced air oven at 120° C. for 2.5 hours. A reference coating derived from a bisphenol-A diepoxide (Epon 1001-O-75, 75% weight in methyl n-amyl ketone, epoxy equivalent weight=450-550 g/eq, received from Momentive) was produced by mixing 10 g of Epon 1001-O-75 with 1.26 g of HMPA, and 6.6 g of 2-butanone using the FlackTek mixer. The coating mixture was cast over six steel Q-panels and one Teflon® coated glass panel. The wet film thickness was approximately 0.2 mm and the film cured in a forced air oven at 120° C. for 2.5 hours.

The cured coatings were characterized using pencil hardness (ASTM D 3363-00), König pendulum hardness (ASTM D 4366-95), mandrel bend test (ASTM D 522-93a), and the crosshatch adhesion test (ASTM D 3359-97). The free film obtained from E-polyAMB/HMPA was characterized using dynamic mechanical analysis (Q800 from TA Instruments). The experiment was carried out from −40° C. to 160° C. using a heating rate of 5° C./min., frequency of 1 Hz, and strain amplitude of 0.02%. The Tg was obtained from the peak maximum in the tan δ response. The values of storage modulus (at 120° C.) and tan δ were found to be 3.05 MPa and 65.2° C., respectively. Tensile testing of dumb bell shaped specimens produced from E-PolyAMB/HMPA according to the ASTM D 638-5 was carried out using an Instron tensile tester fitted with a 100 N load cell. The displacement rate of the movable clamp was set as 1 mm/minute. Data reported was the average of 5 replicate measurements. The values of the Young's modulus (MPa), toughness (mJ), and elongation at break (%) were found to be 2.62±0.3 GPa, 1.4±0.4%, and 0.85±0.36 mJ, respectively. The thermal properties of cured films were determined using differential scanning calorimetry (Q1000 from TA Instruments) by first heating the sample from 30° C. to 120° C. at a heating rate of 10° C./minute ($1^{st}$ heat), cooling from 120° C. to −120° C. at a cooling rate of 10° C./minute (cooling), and reheating from −120° C. to 120° C. at a heating rate 10° C./minute ($2^{nd}$ heat). The Tgs reported from the thermograms obtained from the $2^{nd}$ heat were 46° C. and 40° C. for E-PolyAMB/HMPA and Epon/HMPA, respectively. Table lists the physical properties of these cured coatings.

TABLE XI

Data obtained for cured coatings of E-PolyAMB/HMPA and Epon/HMPA.

| Measurement | E-PolyAMB/ HMPA | Epon/ HMPA |
|---|---|---|
| ASTM Testing of Coated Substrates | | |
| Average thickness (μm) | 39 ± 2 | 45 ± 7 |
| König pendulum hardness (steel substrate), sec. | 190 ± 5 | 193 ± 11 |
| Pencil hardness | 2H | HB |
| Cross hatch adhesion (steel substrate) | 5B | 0B |
| Conical mandrel bend test, Elongation % | 100 | 0 |
| Reverse impact (in-lb) | | |
| MEK double rubs | | |
| Tensile Testing of Free Film Specimens | | |
| Young's modulus (GPa) | 2.62 ± 0.3 | |
| Toughness (mJ) | 0.85 ± 0.36 | |
| Elongation at Break (%) | 1.4 ± 0.4 | |
| Dynamic Mechanical Analysis of Free Films | | |
| Storage modulus at 120° C. (MPa) | 305 | |
| Tg from tanδ (° C.) | 65 | |
| Differential Scanning Calorimetry | | |
| Tg (° C.) | 46 | 40 |

Example 8

Copolymers of AMB and Pentaethylene Glycol
Ethyl Vinyl Ether

Pentaethylene glycol ethyl vinyl ether (PEGEVE) was synthesized using a two step process. First, 20 g of triethylene glycol monoethyl ether (TEGMEE, >98% purity from TCI America), 8.1 g of sodium hydroxide (90%, Sigma-Aldrich), 73 ml of tetrahydrofuran (THF), and 49 ml of DI water were combined in a 500 ml, 3-neck, round-bottom flask using constant stirring to produce a homogeneous solution. The mixture was cooled to 0° C. and then 30.2 g of p-toluenesulfonyl chloride (Aldrich, 99% purity) in 60 ml of TI-IF was added to the reaction mixture drop-wise using an addition funnel and the reaction conducted for 2 hours at 0° C. The reaction mixture was then poured into 100 ml of ice water and the product extracted with methylene chloride. The organic layer was washed with DI water and subsequently dried with anhydrous magnesium sulfate. The product, Ts-TEGMEE, was recovered after evaporation of volatiles under vacuum and dried under vacuum overnight. Next, 2.67 g of sodium hydroxide (Aldrich, 90% purity), 5.17 g of diethylene glycol monovinyl ether (DEGMVE, TCI America), and 10 g of Ts-TEGMEE were combined with 40 ml of THF and 15 ml of DI water in a 500 ml, 3-neck, round-bottom flask equipped with a nitrogen blanket. The temperature was raised to 60° C. with constant stirring. After 24 hours, the reaction mixture was cooled to room temperature and diluted with 150 ml of diethyl ether. The organic layer was washed multiple times with 200 ml of DI water and dried with anhydrous magnesium sulfate. The product, PEGEVE, was collected after evaporation of volatiles under vacuum.

Copolymers of AMB and PEGEVE were produced at 0° C. within a glove box in series of 40 ml vials dried at 200° C. under vacuum just before use. The chemical composition of the polymerization mixtures are described in Table XII. AMB, PEGEVE, IBEA solution (0.28 g/ml in toluene), and MAc were dissolved in dry toluene and chilled to 0° C. Each polymerization was initiated with the addition of ethylaluminum sesquichloride solution (25 wt. % in toluene). After 8 hours, each polymerization was terminated with the addition of 10 ml of methanol. Each copolymer was isolated by passing the polymer solution in methylene chloride through a column packed with alumina and then evaporating of all the volatiles and drying under vacuum overnight at a temperature of 35° C. Polymer molecular weight was characterized using a high-throughput Symyx Rapid Gel Permeation Chromatography equipped with an evaporative light scattering detector (PL-ELS 1000) and polystyrene standards. Tg of the polymers were determined using differential scanning calorimetry (Q1000 from TA Instruments). The experiment was carried out by first heating the sample from 30° C. to 50° C. at a heating rate of 10° C./minute (1$^{st}$ heat), cooling from 50° C. to –120° C. at a cooling rate of 10° C./minute (cooling), and reheating from –120° C. to 120° C. at a heating rate 10° C./minute (2$^{nd}$ heat). Table XIII lists the number-average molecular weight (Mn) expressed relative to polystyrene standards, molecular weight distribution (MWD), and Tg of the polymers produced.

TABLE XII

Chemical composition of reaction mixtures used to produce polyAMB, polyPEGEVE, and poly(AMB-r-PEGEVE) copolymers.

| Polymer Designation | Wt. of AMB (g) | Wt. of PEGEVE (g) | Wt. of IBEA solution* (mg) | Wt. of MAc (mg) | Wt. of toluene (g) | Wt. of Et$_{1.5}$AlCl$_{1.5}$ solution (µl) |
|---|---|---|---|---|---|---|
| PolyAMB | 1.5 | 0 | 186 | 237 | 7.88 | 88 |
| PolyPEGEVE | 0 | 1.5 | 149 | 190 | 7.88 | 70 |
| Poly(AMB-r-PEGEVE)75-25 | 1.125 | 0.375 | 177 | 226 | 7.88 | 83 |
| Poly(AMB-r-PEGEVE)50-50 | 0.75 | 0.75 | 167 | 213 | 7.88 | 79 |
| Poly(AMB-r-PEGEVE)25-75 | 0.375 | 1.125 | 158 | 202 | 7.88 | 75 |

*IBEA solution was 0.455 g of IBEA in 16 ml of dry toluene.

TABLE XIII

Mn, MWD, and Tg data obtained for the polymers described in Table XII.

| Polymer Designation | Mn | MWD | T$_g$ (DSC), ° C. |
|---|---|---|---|
| Poly(AMB) | 18,300 | 1.40 | 1.1 |
| Poly(VEPEG) | 12,600 | 1.48 | –74.1 |
| Poly(AMB-r-VEPEG)75-25 | 13,500 | 1.51 | –26.4 |
| Poly(AMB-r-VEPEG)50-50 | 14,660 | 1.54 | –49.9 |
| Poly(AMB-r-VEPEG)25-75 | 12,550 | 1.52 | –65.2 |

Example 9

Copolymers of AMB and Cyclohexyl Vinyl Ether

Copolymers of AMB and cyclohexyl vinyl ether (CHVE, TCI America, >95%) were produced at 0° C. within a glove box in series of 40 ml vials dried at 200° C. under vacuum just before use. The chemical composition of the polymerization mixtures are described in Table XIV. AMB, CHVE, IBEA solution (0.28 g/ml in toluene), and MAc were dissolved in dry toluene and chilled to 0° C. Each polymerization was initiated with the addition of ethylaluminum sesquichloride solution (25 wt. % in toluene). After 8 hours, each polymerization was terminated with the addition of 10 ml of methanol, which caused the polymer to precipitate. The precipitated polymers were purified using centrifugation and multiple washings with methanol and the polymers isolated by evaporation of volatiles under vacuum. Polymer molecular weight was characterized using a high-throughput Symyx Rapid Gel Permeation Chromatography equipped with an evaporative light scattering detector (PL-ELS 1000) and polystyrene standards. Tg of the polymers were determined using differential scanning calorimetry (Q1000 from TA Instruments). The experiment was carried out by first heating from 30° C. to 80° C. at a heating rate of 10° C./minute (1$^{st}$ heat), cooling from 80° C. to –120° C. at a cooling rate of 10° C./minute (cooling), and reheating from –120° C. to 120° C. at a heating rate 10° C./minute (2$^{nd}$ heat). The T$_g$ was reported from the thermogram obtained from the 2$^{nd}$ heat. Table XV lists the number-average molecular weight (Mn) expressed relative to polystyrene standards, molecular weight distribution (MWD), and Tg of the polymers produced.

TABLE XIV

Chemical composition of reaction mixtures used to produce polyAMB, polyCHVE, and poly(AMB-r-CHVE) copolymers.

| Polymer Designation | Wt. of AMB (g) | Wt. of CHVE (g) | Wt. of IBEA solution* (mg) | Wt. of MAc (mg) | Wt. of toluene (g) | Wt. of $Et_{1.5}AlCl_{1.5}$ solution (µl) |
|---|---|---|---|---|---|---|
| Poly(AMB) | 1.5 | 0 | 186 | 237 | 7.88 | 88 |
| Poly(CHVE) | 0 | 1.5 | 345 | 440 | 7.88 | 163 |
| Poly(AMB-r-CHVE)75-25 | 1.125 | 0.375 | 226 | 288 | 7.88 | 106 |
| Poly(AMB-r-CHVE)50-50 | 0.75 | 0.75 | 265 | 339 | 7.88 | 125 |
| Poly(AMB-r-CHVE)25-75 | 0.375 | 1.125 | 305 | 390 | 7.88 | 144 |

*IBEA solution represents 0.455 g of IBEA in 16 ml of dry toluene.

TABLE XV

Monomer conversion, Mn, MWD, and Tg data obtained for the polymers described in Table XIV.

| Polymer Designation | Conversion (%) | Mn | MWD | $T_g$ (DSC), °C. |
|---|---|---|---|---|
| PolyAMB | 96 | 18,300 | 1.40 | 1.1 |
| PolyCHVE | 98 | 16,900 | 1.51 | 53.5 |
| Poly(AMB-r-CHVE)75-25 | 94 | 17,560 | 1.42 | 6.3 |
| Poly(AMB-r-CHVE)50-50 | 95 | 18,060 | 1.43 | 13 |
| Poly(AMB-r-CHVE)25-75 | 92 | 18,930 | 1.45 | 34.8 |

Example 10

Copolymers of AMB and 2-(Vinyloxy)Ethyl Soyate 2-(vinyloxy)ethyl soyate (2-VOES) was synthesized as follows: First, 0.42 g of potassium hydroxide was dried an oven at 140° C. for 30 minutes to remove moisture. Then, 15 g of soybean oil, 15 g of ethylene glycol monovinyl ether (TCI America), and the dried potassium hydroxide were mixed together in a two-neck round bottom flask and stirred for 3 hr at 70° C. The reaction mixture was then cooled to room temperature and transferred to a 250 ml separating funnel. 100 ml of n-hexane was added to the separating funnel and the solution washed with acidic, DI water (pH 3-3.5) twice and then washed multiple time with DI water and finally with brine solution. The organic layer was dried over MgSO4 and the product isolated by vacuum stripping volatiles. Yield: 13 g (84%). 1H NMR (400 MHz, CDCl$_3$, TMS): δ (ppm) 6.45 (m, 1H), 5.34 (m, 1.5H), 4.28 (t, 2H), 4.16 (dd, 1H), 4.01 (dd, 1H), 3.85 (t, 2H, =CH—O—CH$_2$—CH$_2$—), 2.76 (m, 1.5H), 2.30 (t, 2H), 2.03 (m, 4H), 1.57 (m, 2H), 1.29 (m, 18H), 0.86-0.97 (m, 3H).

Copolymers of AMB and 2-VOES were produced at 0° C. within a glove box in a series of 40 ml vials dried at 200° C. under vacuum just before use. The chemical composition of the polymerization mixtures are described in Table XVI. AMB, 2-VOES, IBEA solution (0.28 g/ml in toluene), and MAc were dissolved in dry toluene and chilled to 0° C. Each polymerization was initiated with the addition of ethylaluminum sesquichloride solution (25 wt. % in toluene). After 8 hours, each polymerization was terminated with the addition of 10 ml of methanol, which caused the polymer to precipitate. The precipitated polymers were purified using centrifugation and multiple washings with methanol and the polymers isolated by evaporation of volatiles under vacuum. Polymer molecular weight was characterized using a high-throughput Symyx Rapid Gel Permeation Chromatography equipped with an evaporative light scattering detector (PL-ELS 1000) and polystyrene standards. Tg of the polymers were determined using differential scanning calorimetry (Q1000 from TA Instruments). The experiment was carried out by first heating the sample from 30° C. to 50° C. at a heating rate of 10° C./minute (1$^{st}$ heat), cooling from 50° C. to −120° C. at a cooling rate of 10° C./minute (cooling), and reheating from −120° C. to 120° C. at a heating rate 10° C./minute (2$^{nd}$ heat). Table XVII lists the number-average molecular weight (Mn) expressed relative to polystyrene standards, molecular weight distribution (MWD), and Tg of the polymers produced.

TABLE XVI

Chemical composition of reaction mixtures used to produce polyAMB and poly(AMB-r-2-VOES) copolymers.

| Polymer Designation | Wt. of AMB (g) | Wt. of 2-VOES (g) | Wt. of IBEA solution* (mg) | Wt. of MAc (mg) | Wt. of toluene (g) | Wt. of $Et_{1.5}AlCl_{1.5}$ solution (µl) |
|---|---|---|---|---|---|---|
| Poly(AMB) | 1.5 | 0 | 186 | 237 | 7.88 | 88 |
| Poly(AMB-r-2-VOES)75-25 | 1.125 | 0.375 | 170 | 218 | 7.88 | 290 |
| Poly(AMB-r-2-VOES)50-50 | 0.75 | 0.75 | 155 | 198 | 7.88 | 263 |
| Poly(AMB-r-2-VOES)25-75 | 0.375 | 1.125 | 140 | 178 | 7.88 | 237 |

*IBEA solution represents 0.455 g of IBEA in 16 ml of dry toluene.

TABLE XVII

Monomer conversion, Mn, MWD, and Tg data obtained for the polymers described in Table XVI.

| Polymer Designation | Conversion (%) | Mn | MWD | $T_g$ (DSC), °C. |
|---|---|---|---|---|
| Poly(AMB) | 96 | 18,300 | 1.40 | 1.1 |
| Poly(AMB-r-2-VOES)75-25 | 93 | 14,790 | 1.39 | −15.2 |
| Poly(AMB-r-2-VOES)50-50 | 90 | 12,390 | 1.36 | −26.6 |
| Poly(AMB-r-2-VOES)25-75 | 76 | 15,520 | 1.25 | −89.5 |

Example 11

Synthesis of Isoeugenol Vinyl Ether

Isoeugenol vinyl ether was synthesized according to the scheme shown below:

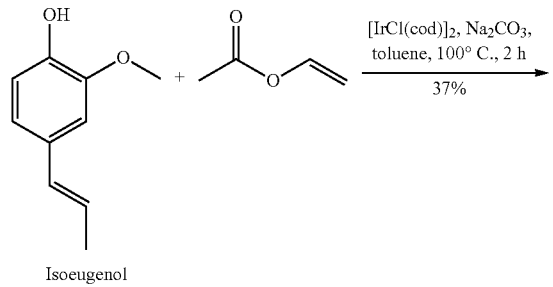

To a mixture of [IrCl(cod)]$_2$ (0.656 mmol) and Na$_2$CO$_3$ (39.36 mmol) in toluene (66 mL) were added isoeugenol (65.6 mmol) and vinyl acetate (131.18 mmol) under N$_2$. The reaction mixture was stirred at 100° C. for 2 h. After quenching with wet ether, the product was isolated by silica gel column chromatography using hexane as the eluent. Isoeugenol vinyl ether was obtained as colorless liquid in 37% yield.

$^1$H NMR (400 MHz, CDCl$_3$) δ 1.89 (m, 3H), 3.85 (s, 3H), 4.35 (m, 1H), 4.64 (m, 1H), 6.13 (m, 1H), 6.34 (dd, J=15.6, 1.2 Hz, 1H), 6.57 (m, 1H), 6.82-6.90 (m, 2H).

Example 12

Synthesis of 4-allyl-2-methoxy-1-(2-(vinyloxy)ethoxy)benzene (AMB)

Materials: Eugenol, 2-Methoxy-4-(2-propenyl)phenol, 99% was obtained from Sigma-Aldrich.

Synthesis of AMB consisted of the preparation of 2-iodoethyl vinyl ether followed by the reaction with eugenol in the presence of potassium hydroxide in methanol. 2-iodoethyl vinyl ether was synthesized using the synthetic scheme shown below:

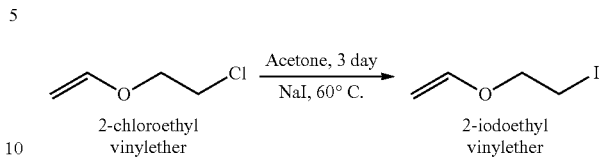

A detailed procedure is as follows: 100.65 g of 2-chloroethyl vinyl ether, 200.16 g of sodium iodide and 730 g of acetone were combined in a 2-liter, 3-neck, round-bottom flask and heated at a temperature of 60° C. for 72 hours. Next, the reaction mixture was cooled to room temperature and diluted with 600 ml of diethyl ether. The organic layer was washed thrice with deionized water and dried with anhydrous magnesium sulfate. The product was recovered by rotary evaporation of diethyl ether and excess 2-chloroethyl vinyl ether at a temperature of 50° C. and a pressure of 60 mmHg for 1 hour. Proton NMR was used to confirm the production of 2-iodoethyl vinyl ether: $^1$H NMR (CDCl$_3$) δ 6.44 ppm (q, 1H, OCH═C), 4.19, 4.05 ppm (dd, 2H, CH$_2$═C), 3.95 ppm (t, 2H, OCH$_2$), 3.3 ppm (t, 2H, CH$_2$I).

Synthesis of 4-allyl-2-methoxy-1-(2-(vinyloxy)ethoxy)benzene (AMB). AMB was synthesized using the synthetic scheme below:

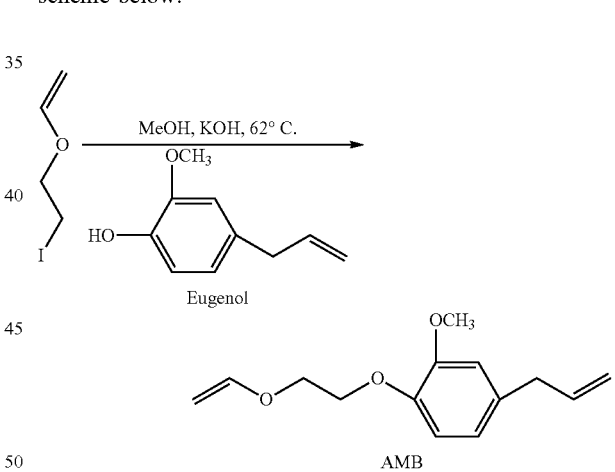

A detailed procedure is as follows: 146.9 g of 2-iodoethyl vinyl ether, 87.4 g of eugenol, 42.7 g of potassium hydroxide, and 500 ml of methanol were combined in a 1000 ml, round-bottom flask fitted with a reflux condenser and stirred at a temperature of 62° C. After 40 hours of reaction, the reaction mixture was cooled to room temperature and diluted with diethyl ether. The organic layer was washed with deionized water thrice and dried with anhydrous magnesium sulfate. The crude product was collected after rotary evaporation of all volatiles at 30° C. for 3 hours. The product, AMB was crystallized from methanol at a temperature of −30° C. and dried under vacuum overnight. Proton NMR was used to confirm the production of AMB: $^1$H NMR (CDCl$_3$) δ 6.5 ppm (q, 1H, OC$\underline{H}$═C), 4.22 ppm-4.25 ppm (m, 2H, C$\underline{H}_2$═C—O), 4.0 ppm-4.2 ppm (m, 4H, C$\underline{H}_2$—CH$_2$), 3.3 ppm (d, 2H, C═C—C$\underline{H}_2$), 5.9 ppm (m, 1H, C═C$\underline{H}$—C), 5.1 (m, 2H, C$\underline{H}_2$═C—C), 3.8 ppm (s, 3H, C$\underline{H}_3$), 6.7 ppm, 6.9 ppm (m, 3H, Ar—$\underline{H}$).

The successful synthesis of AMB was demonstrated using proton NMR, as shown in FIG. 1. One methine and two methylene protons in the vinyl ether double bond appeared at 6.5, 4.22, and 4.2 ppm, respectively.

Example 13

Synthesis of an Initiator for Cationic Polymerization from 4-allyl-2-methoxy-1-(2-(vinyloxy)ethoxy) benzene (AMB)

1-(2-(4-allyl-2-methoxyphenoxy)ethoxy)ethyl acetate (AMEA) was synthesized using the synthetic scheme shown below:

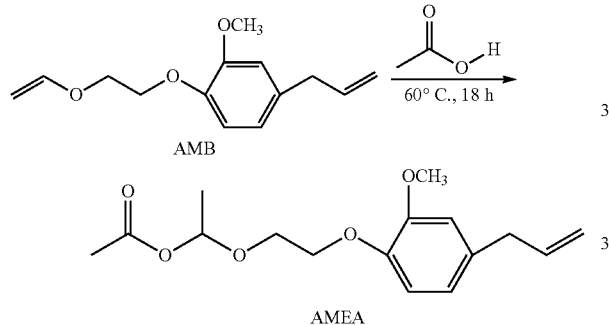

A detailed procedure is as follows: 39.3 g of AMB and 12.2 g of glacial acetic acid were combined in a 250 ml, round-bottom flask fitted with a reflux condenser and stirred at a temperature of 60° C. for 18 hours. The reaction mixture was cooled to room temperature and diluted with diethyl ether. The organic layer was washed with deionized water and dried with anhydrous magnesium sulfate. The crude product was recovered after rotary evaporation of diethyl ether under a reduced pressure at 30° C. The product initiator (AMEA) was separated from the unreacted AMB by passing the crude product through a column packed with silica gel possessing a pore size of 60 Å. The mobile phase was selected as a combination of ethyl acetate and n-hexane (10:90 vol/vol). The pure initiator was collected after rotary evaporation of all volatiles and dried with anhydrous magnesium sulfate before use. Proton NMR, carbon NMR and FTIR were used to confirm the production of AMEA: $^1$H NMR (CDCl$_3$) δ 5.9 ppm (m, 2H, O—C$\underline{H}$—O, C═C$\underline{H}$—C), 1.3 ppm (d, 3H, $\underline{H}_3$C—C—O), 4.03 ppm (t, 2H, C$\underline{H}_2$—CH$_2$), 3.8 ppm (m, 2H, C$\underline{H}_2$—CH$_2$), 3.3 ppm (d, 2H, C═C—C$\underline{H}_2$), 3.7 ppm (s, 3H, $\underline{H}$C$_3$—O), 6.7 ppm, 6.9 ppm (m, 3H, Ar—$\underline{H}$), 1.9 ppm (s, 3H, C$\underline{H}_3$—C═O).

Example 14

Exemplary Living Carbocationic Polymerization of a Vinyl Ether Monomer Using 1-(2-(4-allyl-2-methoxyphenoxy)ethoxy)ethyl acetate (AMEA) as an Initiator What follows is an example of carbocationic polymerization of a vinyl ether monomer using 1-(2-(4-allyl-2-methoxyphenoxy)ethoxy)ethyl acetate (AMEA) as a functionalized initiator for the polymerization of a vinyl ether monomer. The use of AMEA as the initiator enables the production of block and graft copolymers by utilizing the allyl group derived from AMEA. The scheme below illustrates the synthesis of poly(2-chlorovinyl ether) possessing an allyl group at one chain end, which was derived from AMEA:

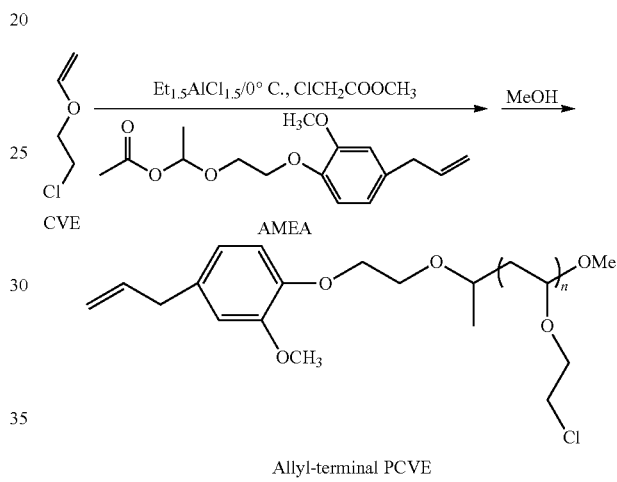

Allyl-terminal PCVE

Chloroethyl vinyl ether (CVE) and toluene were distilled over calcium hydride before use. Polymerizations were carried out in a series of dry test tubes partially immersed in a heptane bath at 0° C. inside a glove box. In each test tube, 30.4 mg of AMEA, 2.2 g of CVE ([CVE]$_0$:[AMEA]$_0$=200:1), and 2.8 g of methyl chloroacetate (MCAc) ([CVE]$_0$:[MCAc]$_0$=200:250) were dissolved in 6.36 g of dry toluene and chilled to 0° C. Each polymerization was initiated by the addition of 256 mg of supplied ethylaluminum sesquichloride solution ([CVE]$_0$:[Et$_{1.5}$AlCl$_{1.5}$]$_0$=200:5). Each reaction was terminated after predetermined interval times by the addition of 15 ml of chilled methanol, which caused the polymer to precipitate. The polymer was isolated and washed multiple times with methanol using centrifugation. The purified polymer was collected as a viscous liquid after centrifugation at 4500 rpm at a temperature of 21° C. for 10 minutes and drying under vacuum overnight. The percentage of conversion of each polymerization was calculated gravimetrically and the number average molecular weight was measured using gel permeation chromatography.

Figure 2:
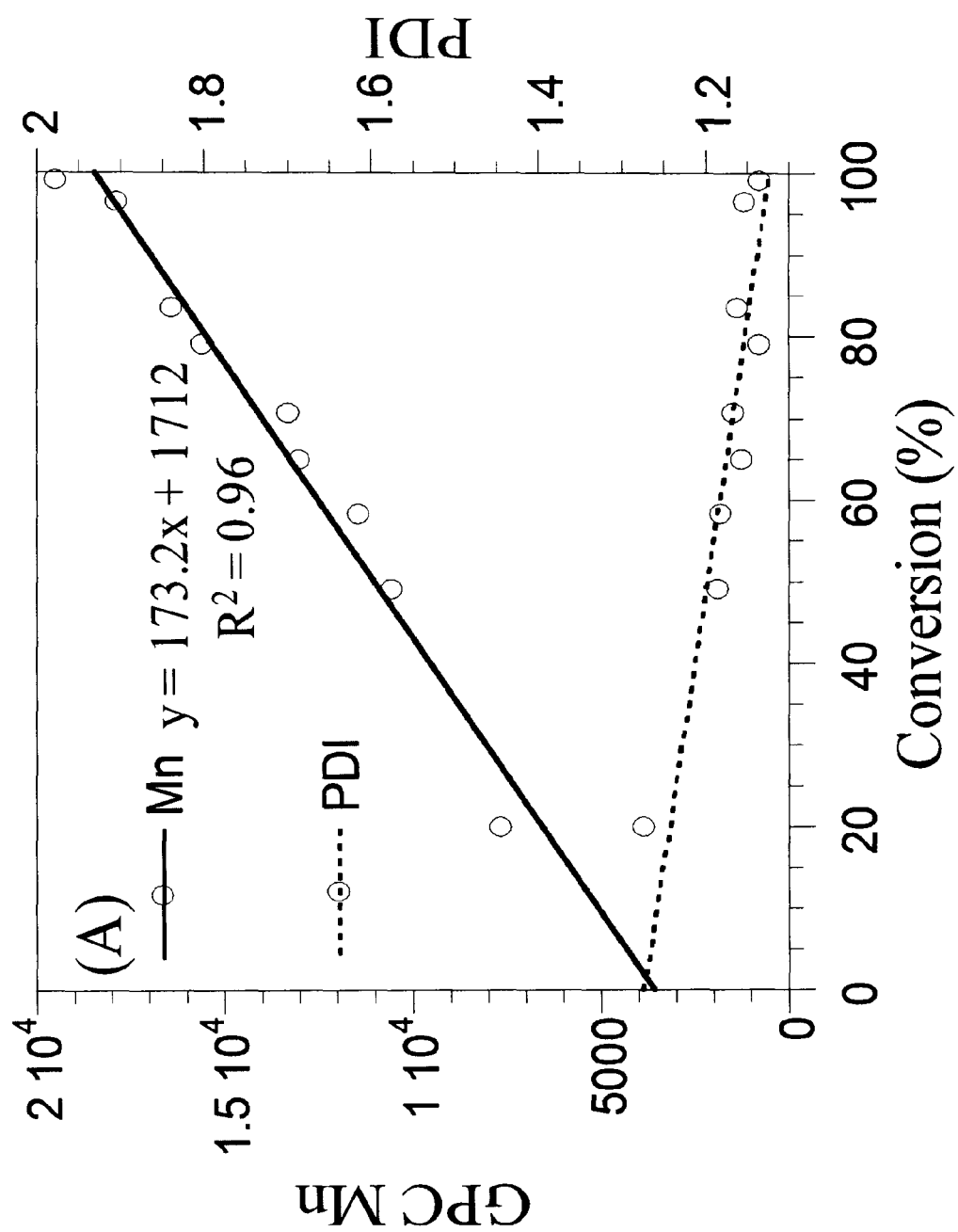
FIG. 2 shows molecular weight and polydispersity index as a function of conversion percentage for polymerization of chloroethyl vinyl ether.

As shown in FIG. 2, molecular weight increased linearly with CVE conversion and polydispersity index (PDI) of the polymer samples was relatively low, which suggests that the polymerization was living.

Synthesis of PCVE Possessing a Theoretical Degree of Polymerization of 50

53.35 g of CVE, 2.95 g of AMEA, 65.8 ml of MCAc ($[CVE]_0:[AMEA]_0:[MCAc]_0=50:1:75$) were dissolved in 154 g of dry toluene and taken in a 500 ml round bottom flask. The solution was cooled to 0° C. and the reaction was started by the addition of 9.9 g of supplied ethylaluminum sesquichloride solution ($[CVE]_0:[Et_{1.5}AlCl_{1.5}]_0=50:2$). After 32 minutes of reaction, the reaction mixture was terminated by the addition of 350 ml of chilled methanol, which caused the polymer to precipitate. The polymer was isolated and washed multiple times with methanol using centrifugation. The purified polymer was collected as a viscous liquid after centrifugation at 4500 rpm at a temperature of 21° C. for 10 minutes and drying under vacuum overnight. The percentage of conversion was calculated gravimetrically and the number average molecular weight was measured using gel permeation chromatography.

Example 15

Synthesis of a Poly(Dimethylsiloxane) (PDMS)-Based Block Copolymer Using a Vinyl Ether Polymer with an Allyl Group at One Chain End Derived from Using 1-(2-(4-allyl-2-methoxyphenoxy)ethoxy)ethyl acetate (AMEA) as an Initiator and Hydrosilylation to Couple Polymer Chains The synthesis procedure for producing a poly(2-chloroethyl vinyl ether-b-poly(dimethyl siloxane)-b-poly(2-chloroethyl vinyl ether) triblock copolymer (PCVE-b-PDMS-b-PCVE) is shown below:

A detailed procedure is as follows: PCVE and hydride-terminated PDMS (PDMS/H) were combined together in a dry one liter round bottom flask inside a glove box according to the formulation in Table XVIII:

TABLE XVIII

Formulation table for the synthesis of PCVE-b-PDMS-b-PCVE.

| PDMS-b-PCVE | Wt of PCVE, (g) | Wt. of PDMS/H-1.05K (DMS-H11 from Gelest), (g) | Wt. of PDMS/H-17.2K (DMS-H25 from Gelest), (g) | Ratio of PCVE:PDMS (Wt. %) |
|---|---|---|---|---|
| PDMS-1.05K | 40 | 4.17 | — | 90.6:9.4 |
| PDMS-17.2K | 40 | — | 65.22 | 38:62 |

Polymers were dissolved by the addition of toluene and the final concentration of the reaction mixture was maintained as 16 weight percent solids. The reaction was started by the addition of 270 mg of platinum oxide and heating at a temperature of 90° C. The completion of hydrosilylation was monitored using proton NMR and FTIR. The reaction was continued for 4 days until the Si—H protons at 4.7 ppm and allyl protons at 5.1 ppm were totally absent in a proton NMR spectrum of PCVE-b-PDMS-b-PCVE. The reaction was then cooled to room temperature and the platinum oxide was vacuum filtered through a silica bed. The PCVE-b-PDMS-b-PCVE was precipitated into methanol and dried under vacuum overnight.

Synthesis of an Antimicrobial Polymer by Quaternization of a PCVE-b-PDMS-b-PCVE Triblock Copolymer The procedure for producing quaternized PCVE-b-PDMS-b-PCVE triblock copolymers is illustrated below:

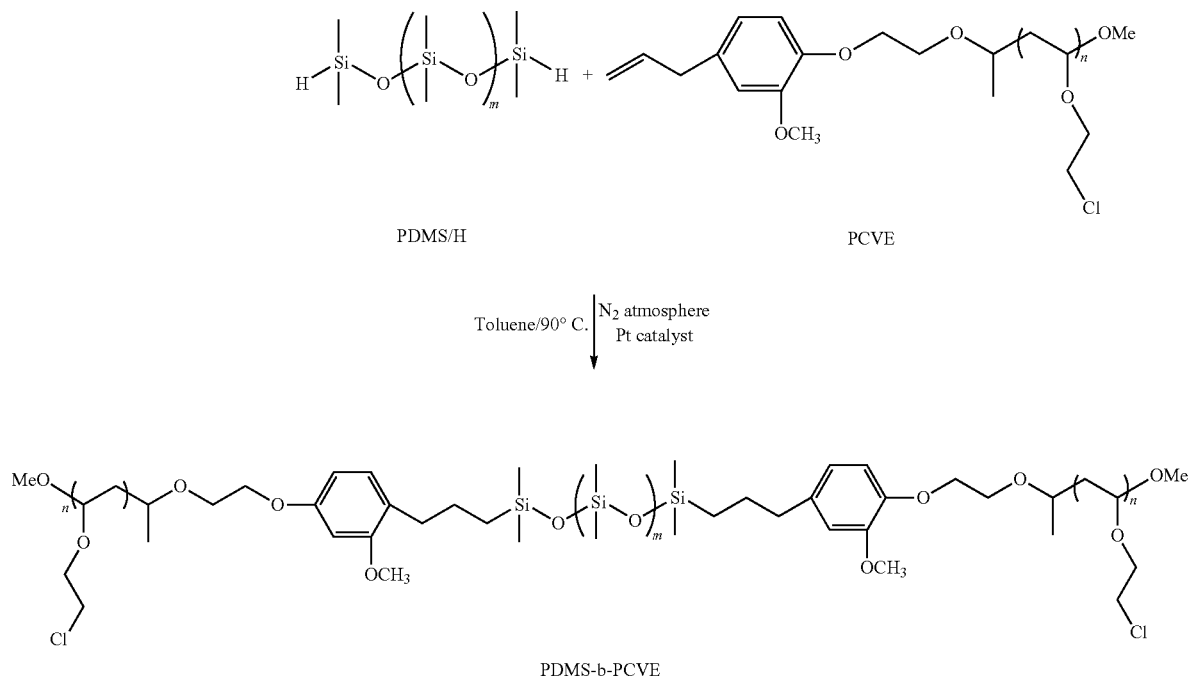

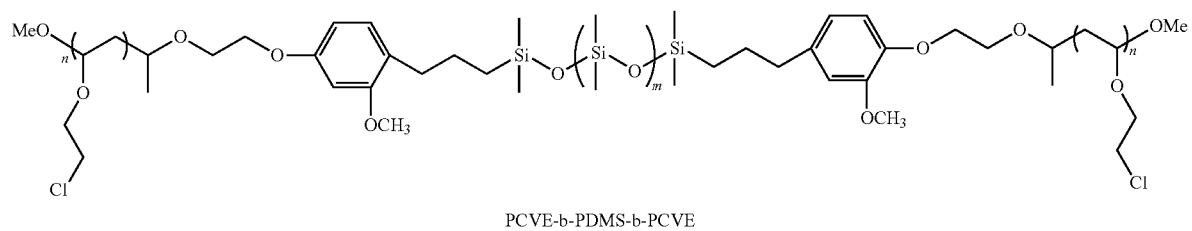

PCVE-b-PDMS-b-PCVE

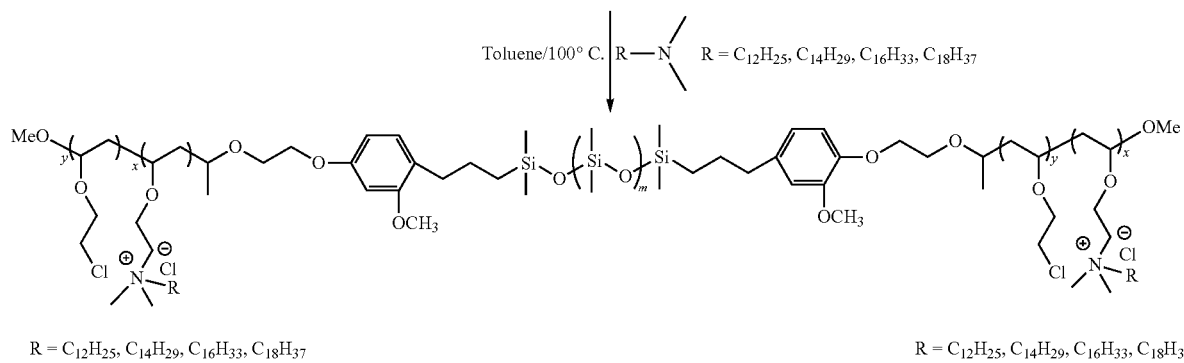

R = $C_{12}H_{25}$, $C_{14}H_{29}$, $C_{16}H_{33}$, $C_{18}H_{37}$

R = $C_{12}H_{25}$, $C_{14}H_{29}$, $C_{16}H_{33}$, $C_{18}H_{37}$

A detailed procedure is as follows: PCVE-b-PDMS-b-PCVE and a tertiary amine were combined in a 40 ml vial and dissolved with toluene at a concentration of 5 weight percent solids. A series of such solutions was produced by varying the n-alkyl chain lengths and concentration of the tertiary amine. Four different tertiary amines, namely, N,N-dimethyldodecylamine (C-12), N,N-dimethyltetradecylamine (C-14), N,N-dimethylhexadecylamine (C-16), and N,N-dimethyloctadecylamine (C-18) were used. For each amine, three different concentrations were used to replace the chlorine atoms in PCVE-b-PDMS-b-PCVE by 10 mole %, 30 mole %, and 50 mole %. Thus, a total of 12 polymer solutions were produced from each PCVE-b-PDMS-b-PCVE. The compositions of the reaction mixtures are described in Tables XIX and XX:

TABLE XIX

Formulation table for the quaternization of PCVE-b-PDMS-b-PCVE synthesized from PDMS/H-1.05K.

| PDMS-b-PCVE-b-PQ | Wt. of PDMS-1.05K (g) | Wt. of C-12 amine (g) | Wt. of C-14 amine (g) | Wt. of C-16 amine (g) | Wt. of C-18 amine (g) |
|---|---|---|---|---|---|
| PDMS-1.05K-C12-10% | 1.5 | 0.281 | — | — | — |
| PDMS-1.05K-C12-30% | 1.5 | 0.842 | — | — | — |
| PDMS-1.05K-C12-50% | 1.5 | 1.403 | — | — | — |
| PDMS-1.05K-C14-10% | 1.5 | — | 0.324 | — | — |
| PDMS-1.05K-C14-30% | 1.5 | — | 0.973 | — | — |
| PDMS-1.05K-C14-50% | 1.5 | — | 1.621 | — | — |
| PDMS-1.05K-C16-10% | 1.5 | — | — | 0.362 | — |
| PDMS-1.05K-C16-30% | 1.5 | — | — | 1.086 | — |
| PDMS-1.05K-C16-50% | 1.5 | — | — | 1.809 | — |
| PDMS-1.05K-C18-10% | 1.5 | — | — | — | 0.447 |
| PDMS-1.05K-C18-30% | 1.5 | — | — | — | 1.34 |
| PDMS-1.05K-C18-50% | 1.5 | — | — | — | 2.23 |

TABLE XX

Formulation table for the quaternization of PCVE-b-PDMS-b-PCVE synthesized from PDMS/H-17.2K.

| PDMS-b-PCVE-b-PQ | Wt. of PDMS-17.2K (g) | Wt. of C-12 (g) | Wt. of C-14 (g) | Wt. of C-16 (g) | Wt. of C-18 (g) |
|---|---|---|---|---|---|
| PDMS-17.2K-C12-10% | 1.5 | 0.119 | — | — | — |
| PDMS-17.2K-C12-30% | 1.5 | 0.357 | — | — | — |
| PDMS-17.2K-C12-50% | 1.5 | 0.596 | — | — | — |
| PDMS-17.2K-C14-10% | 1.5 | — | 0.138 | — | — |
| PDMS-17.2K-C14-30% | 1.5 | — | 0.413 | — | — |
| PDMS-17.2K-C14-50% | 1.5 | — | 0.688 | — | — |
| PDMS-17.2K-C16-10% | 1.5 | — | — | 0.154 | — |
| PDMS-17.2K-C16-30% | 1.5 | — | — | 0.461 | — |
| PDMS-17.2K-C16-50% | 1.5 | — | — | 0.768 | — |
| PDMS-17.2K-C18-10% | 1.5 | — | — | — | 0.189 |
| PDMS-17.2K-C18-30% | 1.5 | — | — | — | 0.568 |
| PDMS-17.2K-C18-50% | 1.5 | — | — | — | 0.947 |

Example 16

Copolymers of AMB and Triethylene Glycol Ethyl Vinyl Ether (TEGEVE)

Triethylene glycol ethyl vinyl ether (TEGEVE) was synthesized using a two step process. First, 40.2 g (0.3 mol) of diethylene glycol monoethyl ether (DEGMEE, >98% purity from Aldrich), 12.6 g of sodium hydroxide (90%, Sigma-Aldrich), 160 ml of tetrahydrofuran (THF), and 40 ml of DI water were combined in a 500 ml, 3-neck, round-bottom flask using constant stirring to produce a homogeneous solution. The mixture was cooled to 0° C. and then 55.6 g (0.28 mol) of p-toluenesulfonyl chloride (Aldrich, 99% purity) in 200 ml of THF was added to the reaction mixture drop-wise using an addition funnel and the reaction conducted for 2 hours at 0° C. and then overnight at room temperature. The reaction mixture was then poured into 200 ml of ice water and the product extracted with methylene chloride (150 ml×3). The organic layer was washed with DI water and subsequently dried with anhydrous magnesium sulfate. The tosyl compound was recovered after evaporation of volatiles under vacuum and dried under vacuum overnight. Yield: 65.6 g. $^1$H NMR (400 MHz, CDCl$_3$, TMS): δ (ppm) 7.75 (d, 8 Hz, 2H); 7.30 (d, 8 Hz, 2H); 4.12 (t, 4 Hz, 2H); 3.65 (t, 4 Hz, 2H); 3.54-3.51 (m, 2H); 3.48-3.42 (m, 4H); 2.40 (s, 3H); 1.15 (t, 8 Hz, 3H).

Next, 8.8 g (0.1 mol) of ethylene glycol monovinyl ether (EGMVE) in 100 ml of THF was added dropwise to a suspension of NaH (60% dispersion in mineral oil) (4.45 g) in 150 mL of TI-IF at 0° C. This mixture was stirred for a 2 hrs at 0° C. and then a solution of the tosyl compound (28.9 g, 0.1 mol) in 100 mL of THF was added dropwise. The solution was allowed to warm to room temperature and then heated at 60° C. overnight. The solid precipitate was filtered off and all volatile materials were removed by rotory evaporation. The yellow oil was dissolved into toluene (200 mL) and the organic layer wash with 3×150 mL of water. The aqueous layer was then next extracted with 2×50 mL of chloroform to recover any product that may have been present in the aqueous layer. All the organic layers were combined, dried with MgSO$_4$, and the solvent removed by rotary evaporation. Yield: 19.3 g. $^1$H NMR (400 MHz, CDCl$_3$, TMS): δ (ppm) 6.46 (q, 8 Hz, 1H); 4.15 (dd, 14 Hz & 2 Hz, 1H); 3.97 (dd, 8 Hz & 2 Hz, 1H); 3.81 (t, 4 Hz, 2H), 3.71 (t, 4 Hz, 2H); 3.65-3.60 (m, 6H); 3.55 (t, 4 Hz, 2H); 3.49 (q, 8 Hz, 2H); 1.17 (t, 8 Hz, 3H).

A copolymer of AMB and TEGEVE (75:25 Mole ratio) was produced at 0° C. within a glove box in a 250 ml round-bottom flask dried at 200° C. under vacuum just before use. AMB (11.7 g, 0.05 M), TEGEVE (3.07 g, 0.0167 M), and IBEA solution (1 ml, 0.2 M in toluene) were dissolved in dry toluene (60 ml) and chilled to 0° C. The polymerization was initiated with the addition of ethylaluminum sesquichloride solution (2.0 ml, 25 wt. % in toluene). After 16 hours, the polymerization was terminated with the addition of 10 ml of methanol. The volume of the solution was reduced to 50% using a rotary evaporator and the copolymer isolated by precipitation into methanol. The copolymer was then dissolved in minimum volume of chloroform and re-precipitated into methanol. The purified polymer was then dried under vacuum overnight at a temperature of 35° C. Polymer molecular weight was characterized using a high-throughput Symyx Rapid Gel Permeation Chromatography System equipped with an evaporative light scattering detector (PL-ELS 1000) and polystyrene standards. $M_n$, 7,700 (MWD, 1.68). Tg of the polymer was determined using differential scanning calorimetry (Q1000 from TA Instruments). The experiment was carried out by first heating the sample from 30° C. to 150° C. at a heating rate of 20° C./minute (1st heat), cooling from 150° C. to −100° C. at a cooling rate of 20° C./minute (cooling), and reheating from −100° C. to 150° C. at a heating rate 20° C./minute (2nd heat). $T_g$ (DSC), ° C. (−6.99).

Example 17

Copolymers of AMB and Tetraethylene Glycol Methyl Vinyl Ether (TEGMVE) and their Use for the Production Siloxane-Based Coatings for Potential Application as Fouling-Release Coatings for Ship Hulls Tetraethylene glycol methyl vinyl ether (TEGMVE) was synthesized using a two step process. First, 16.42 g (0.1 mol) of triethylene glycol monomethyl ether (TEGMME, >98% purity from TCI America), 4.2 g of sodium hydroxide (90%, Sigma-Aldrich), 70 ml of tetrahydrofuran (THF), and 30 ml of DI water were combined in a 500 ml, 3-neck, round-bottom flask using constant stirring to produce a homogeneous solution. The mixture was cooled to 0° C. and then 18.5 g (0.097 mol) of p-toluenesulfonyl chloride (Aldrich, 99% purity) in 50 ml of THF was added to the reaction mixture drop-wise using an addition funnel and the reaction conducted for 2 hours at 0° C. and then overnight at room temperature. The reaction mixture was then poured into 100 ml of ice water and the product extracted with methylene chloride (50 ml×3). The organic layer was washed with DI water and subsequently dried with anhydrous magnesium sulfate. The product, Ts-TEGME, was recovered after evaporation of volatiles under vacuum and dried under vacuum overnight. Yield: 26.6 g. $^1$H NMR (400 MHz, CDCl$_3$, TMS): δ (ppm) 7.76 (d, 8 Hz, 2H); 7.31 (d, 8 Hz, 2H); 4.13 (t, 6 Hz, 2H); 3.65 (t, 6 Hz, 2H); 3.59-3.56 (m, 6H); 3.51-3.48 (m, 2H); 3.34 (s, 3H); 2.42 (s, 3H).

Next, 2.64 g (0.03 mol) of ethylene glycol monovinyl ether (EGMVE) in 40 ml of THF was added dropwise to a suspension of NaH (60% dispersion in mineral oil) (1.5 g, 0.037 mol) in 40 mL of THF at 0° C. This mixture was stirred for a 2 hrs at 0° C. and then a solution of Ts-TEGME (9.55 g, 0.03 mol) in 30 mL of THF was added dropwise. The solution was allowed to warm to room temperature and then heated at 60° C. overnight. The solid precipitate was filtered off and all volatile materials were removed under vacuum. The yellow oil was dissolved in toluene (100 mL) and the organic layer washed with 3×100 mL of water. Next, the aqueous layer was extracted with 2×50 mL of chloroform to recover any product that may have been retained in the aqueous layer. The organic layers (i.e. toluene and chloroform) were combined, dried with MgSO4, and the solvent removed by rotary evaporation. Yield: 5.1 g. $^1$HNMR (400 MHz, CDCl$_3$, TMS): δ (ppm) 6.45 (q, 8 Hz, 1H); 4.14 (dd, 14 Hz & 2 Hz, 1H); 3.97 (dd, 8 Hz & 2 Hz, 1H); 3.80 (t, 4 Hz, 2H); 3.69 (t, 4 Hz, 2H); 3.65-3.59 (m, 10H); 3.51 (t, 4 Hz, 2H); 3.34 (s, 3H).

Copolymers of AMB and TEGMVE and well as the homopolymer of AMB (polyAMB) were produced at 0° C. within a glove box in a 250 ml round-bottom flask dried at 200° C. under vacuum just before use. The chemical composition of the polymerization mixtures are described in Table XXI. AMB, TEGMVE, and IBEA solution were dissolved in dry toluene and chilled to 0° C. Each polymerization was initiated with the addition of ethylaluminum sesquichloride solution (25 wt. % in toluene). After 16 hours, each polymerization was terminated with the addition of 10 ml of methanol. The volumes of the solutions were reduced to 50% using rotary evaporator and then the copolymers were isolated by precipitation into methanol. The isolated copolymers were then dissolved in a minimum volume of chloroform and re-precipitated into methanol. Copolymers were dried under vacuum overnight at a temperature of 35° C. Polymer molecular weight was characterized using a high-throughput Symyx Rapid Gel Permeation Chromatography System equipped with an evaporative light scattering detector (PL-ELS 1000) and polystyrene standards. Tg of the polymers were determined using differential scanning calorimetry (Q1000 from TA Instruments). The experiment was carried out by first heating samples from 30° C. to 150° C. at a heating rate of 20° C./minute (1st heat), cooling from 150° C. to −100° C. at a cooling rate of 20° C./minute (cooling), and reheating from −100° C. to 150° C. at a heating rate 20° C./minute (2nd heat). Table XXII lists the number-average molecular weight (Mn), expressed relative to polystyrene standards, molecular weight distribution (MWD), and Tg of the polymers produced.

TABLE XXI

Chemical composition of reaction mixtures used to produce polyAMB, and poly(AMB-r-TEGMVE) copolymers.

| Polymer Designation | Amount of AMB (g) | Amount TEGMVE (g) | Amount IBEA solution* (ml) | Amount toluene (ml) | Amount $Et_{1.5}AlCl_{1.5}$ solution (ml) | Yield (g) |
|---|---|---|---|---|---|---|
| PolyAMB | 15.6 | 0 | 1.0 | 60 | 2.0 | 14.2 |
| Poly(AMB-r-TEGMVE)90-10 | 14.04 | 1.56 | 1.0 | 60 | 2.0 | 14.2 |
| Poly(AMB-r-TEGMVE)75-25 | 11.7 | 3.9 | 1.0 | 60 | 2.0 | 14.7 |
| Poly(AMB-r-TEGMVE)50-50 | 7.72 | 7.72 | 1.0 | 60 | 2.0 | 15.0 |

*IBEA solution was 0.2M in Toluene.

TABLE XXII

Monomer conversion, Mn, MWD, and Tg data obtained for the polymers described in Table XXI.

| Polymer Designation | Conversion (%) | Mn | MWD | $T_g$ (DSC), °C. |
|---|---|---|---|---|
| Poly(AMB) | 91 | 33,500 | 1.67 | 7.2 |
| Poly(AMB-r-TEGMVE)90-10 | 91 | 21,500 | 1.54 | -2.8 |
| Poly(AMB-r-TEGMVE)75-25 | 94 | 27,200 | 1.54 | -12.6 |
| Poly(AMB-r-TEGMVE)50-50 | 97 | 13,000 | 1.91 | -35.3 |

Synthesis of Monohydride-Functional Polydimethylsiloxane (MHT-PDMS)

Monohydride-terminated polydimethylsiloxane (MHT-PDMS) was synthesized as illustrated below:

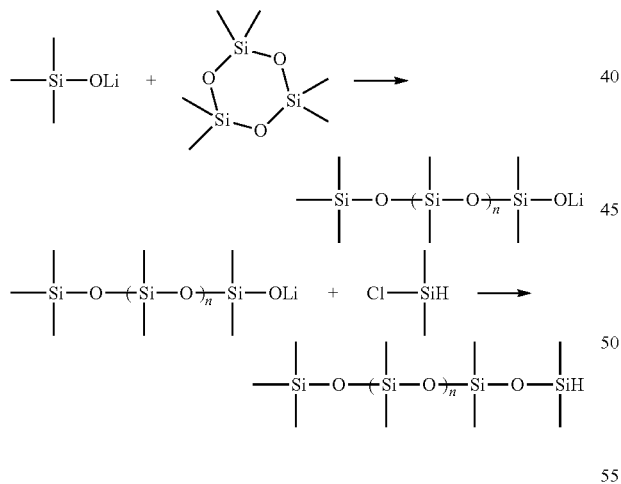

A detailed procedure is as follows: 50 g (0.22 M) of hexamethylcyclotricycloxane ($D_3$) (Aldrich) was dissolved in 50 ml of THF. The solution was degassed by purging with nitrogen gas for 15 minutes. Lithium trimetylsilanolate (0.96 g, 10 mmol) (Aldrich) was added to the solution to initiate polymerization at room temperature. The mixture was stirred at room temperature for 24 hours. The solution was cooled to 0° C. and 1.90 g of dimethylchlorosilane (Aldrich) was added. The solution was rotary evaporated to remove THF and a lithium chloride salt precipitate was formed. The lithium chloride salt was removed by vacuum filtration to yield MHT-PDMS. Yield: 46.2 g. $^1$H NMR (400 MHz, CDCl$_3$, TMS): δ (ppm) 4.70 (m, Si—H); 0.07 (s, Me). Molecular weight based on NMR. 7900, GPC ($M_n$ 7700, PDI 1.17).

Synthesis of PolyAMB with PDMS Grafts

As illustrated below, PMDS grafts were attached to polyAMB using hydrosilylation:

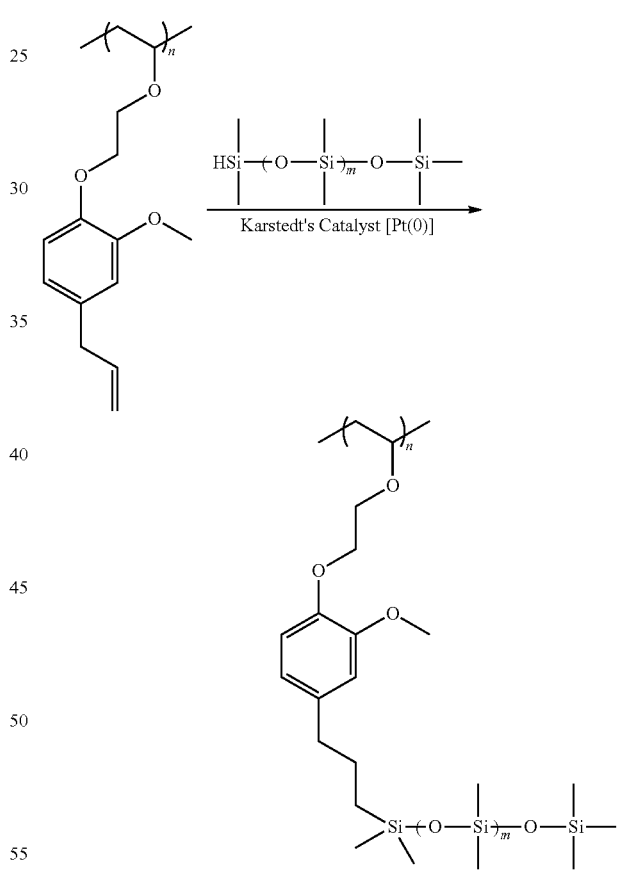

14.04 g (60 mmol) of polyAMB (described in Table XXI) and 150 ml of dry toluene were added to a two-neck, 250 ml, round-bottom flask. The mixture was heated to 40° C. under stirring to dissolve the polymer. The solution was degassed for 15 minutes by purging with nitrogen. 0.10 g of Karstedt's catalyst was added and the solution stirred at 40° C. for 20 minutes. The MHT-PDMS (3.50 g, 25% by weight) was added and the mixture stirred at 40° C. for 16 h. The solution was cooled to room temperature and the volume was reduced to 50% using a rotary evaporator. The mixture was then added to rapidly stirring methanol (250 ml) which caused the polymer to precipitate. The polymer was then dissolve in minimum volume of chloroform and re-precipitated into methanol. Finally, the polymer was dried under vacuum. Yield: 14.2 g (79%). $^1$H NMR (400 MHz, CDCl$_3$, TMS): δ (ppm) 6.68-6.53 (m, 3H); 5.94-5.81 (m, 1H); 4.99 (bs, 2H); 3.94 (bs, 2H); 3.70 (bs 6H); 3.22 (bs, 2H); 1.66 (bs, 2H); 0.06 (s, 4.5H). $T_g$ (DSC) 6° C.

Synthesis of a Graft Copolymer Based on Poly(AMB-r-TEGMVE)75-25 and MHT-PDMS

The graft copolymer illustrated below was synthesized in the same fashion as the polyAMB-g-PDMS graft copolymer previously described. The only exception to the procedure was that poly(AMB-r-TEGMVE)75-25 (described in Table XXI) was used in place of polyAMB. Yield: 73%. $^1$H NMR (400 MHz, CDCl$_3$, TMS): δ (ppm) 6.72-6.54 (m, 3H); 5.86 (bs, 1H); 5.00 (bs, 2H); 3.94-3.23 (bs, 15H); 1.64 (bs, 2H); 0.06 (bs, 7H). $T_g$ (DSC) –9.0° C.

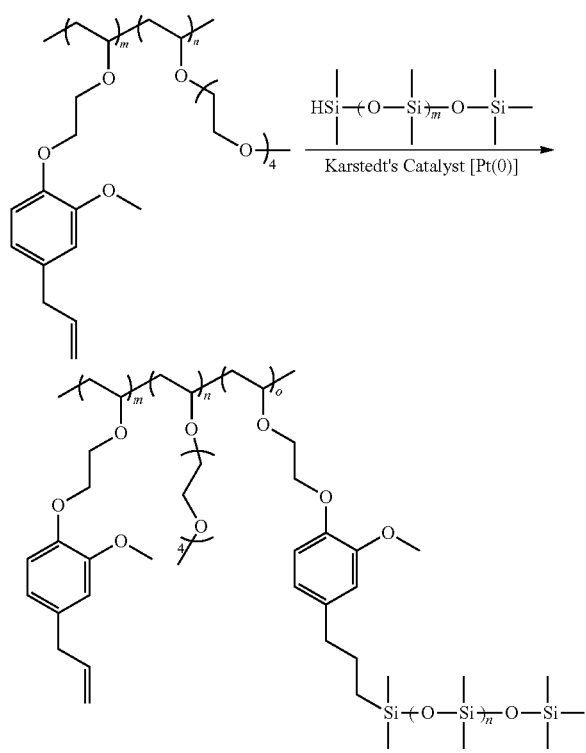

Addition-Cured Siloxane Coatings Containing Graft Copolymers Based on PolyAMB or Poly(AMB-r-TEGMVE)75-25

The polyAMB-g-PDMS graft copolymer and poly(AMB-r-TEGMVE)75-25-g-PDMS graft copolymer described above were incorporated into an addition-curable, siloxane-based coating for potential application as a fouling-release coating to combat biofouling of ship hulls. Six coatings were produced as follows: First, three stock solutions were prepared. Stock solution 1 comprised a solution blend of 54.8 g of SILASTIC® T-2 Base (Dow Corning) and 54.7 g of SW Reducer 15 (Sherwin-Williams). Stock solution 2 was derived from a mixture of 4.4 g of polyAMB-g-PDMS graft copolymer and 17.7 g of SW Reducer 15 (Sherwin-Williams), while stock solution 3 was derived from a mixture of 3.9 g of poly(AMB-r-TEGMVE)75-25-g-PDMS graft copolymer and 15.5 g of SW Reducer 15 (Sherwin-Williams). The six coating solutions produced are described in Table XXIII. All of the coatings cured into tack-free films when allowed to sit at room temperature.

TABLE XXIII

Compositions of addition-cured polysiloxane-based coatings containing the polyAMB-g-PDMS graft copolymer or poly(AMB-r-TEGMVE)75-25-g-PDMS graft copolymer. All values are weight percent.

| Coating Label | Stock solution 1 | Stock solution 2 | Stock solution 3 | SILASTIC ® T-2 Curing Agent (Dow Corning) |
|---|---|---|---|---|
| 1 | 26 | 66 | — | 8 |
| 2 | 26 | — | 66 | 8 |
| 3 | 20 | 72 | — | 8 |
| 4 | 20 | — | 72 | 8 |
| 5 | 14 | 78 | — | 8 |
| 6 | 14 | — | 78 | 8 |

Moisture-curable compositions based on polyAMB, poly(AMB-r-TEGMVE)90-10, poly(AMB-r-TEGMVE)75-25, and poly(AMB-r-TEGMVE)50-50, which are described in Table XXI, were produced using the synthetic scheme shown below:

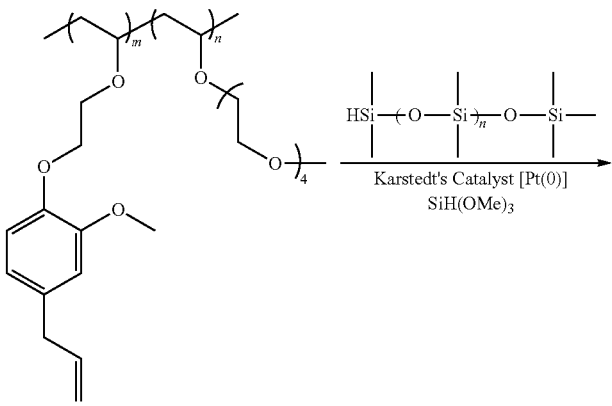

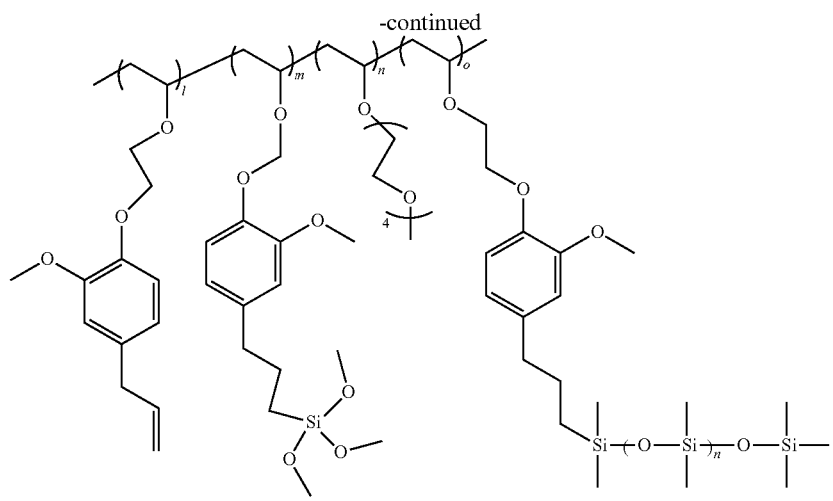

The synthetic procedure was as follows: For each of the four polymers [polyAMB, poly(AMB-r-TEGMVE)90-10, poly(AMB-r-TEGMVE)75-25, and poly(AMB-r-TEGMVE)50-50]. 3.51 g (15 mmol) of polymer and 18 ml of chloroform were combined in a 40 ml glass vial inside a glove box. The mixture was heated at 40° C. with stirring to dissolve the polymer. Two drops of Karstedt's catalyst was added and stirring continued at 40° C. for 20 minutes. Next, the MHT-PDMS previously described (0.877 g, 25% by weight) and trimethoxysilane (0.336 g, 3 mmol, from Gelest) were added and the mixture stirred at 40° C. for 16 h. The polymer solutions produced were used for the production of moisture-curable coatings by adding tetrabutylammonium fluoride (TBAF) as a catalyst for condensation reactions. TBAF, obtained from Aldrich Chemical as a 1M solution in xylene, was diluted to 0.1M with toluene. 150 mg of the 0.1M TBAF was added into each of the reaction mixtures described above and mixed using a vortex mixer. The coating solutions (300 μl for each) were deposited over primed aluminum discs placed inside wells of a microtiter plate. Coatings were cured at room temperature. The fouling-release properties of coatings based on polyAMB and poly(AMB-r-TEGMVE)90-10 were characterized using the marine bacterium, *Cellulophaga lytica*, and the algal species, *Navicula incerta*, and the characterization methods described in Chisholm and Christianson PCT Int. Appl. (2011) WO 2011069111 A1 20110609. Table XXIV lists the percent biofilm removal from the two coatings of the invention to that for a commercially available silicone elastomer, namely, SILASTIC® T-2 from Dow Corning. As shown in Table XXIV, the coatings based on the polymers of the invention provided much easier removal of biofilms of the marine bacterium, *C. lytica*.

TABLE XXIV

Fouling-release data for moisture-curable coatings based on polyAMB and poly(AMB-r-TEGMVE)90-10.

| Coating | *C. lytica* removal at a water pressure of 10 psi | *C. lytica* removal at a water pressure of 20 psi | *N. incerta* removal at a water pressure of 10 psi | *N. incerta* removal at a water pressure of 20 psi |
|---|---|---|---|---|
| SILASTIC ® T-2 | 56.6% | 68.1% | 23.7% | 50.6% |
| Coating based on polyAMB | 87.4% | 97.0% | 34.7% | 40% |

TABLE XXIV-continued

Fouling-release data for moisture-curable coatings based on polyAMB and poly(AMB-r-TEGMVE)90-10.

| Coating | *C. lytica* removal at a water pressure of 10 psi | *C. lytica* removal at a water pressure of 20 psi | *N. incerta* removal at a water pressure of 10 psi | *N. incerta* removal at a water pressure of 20 psi |
|---|---|---|---|---|
| Coating based on poly(AMB-r-TEGMVE)90-10 | 85.1% | 82.7% | 22% | 33.9% |

Example 18

Overview of Production of Monomers and Polymers Incorporating Cardanol

Cardanol is a compound derived from anacardic acid, which is the main component of cashew nutshell liquid. The alkyl chain of cardanol can contain 0, 1, 2 or 3 double bonds. The chemical structure of a triply unsaturated form of cardanol having a $C_{15}H_{25}$ alkyl chain is shown below:

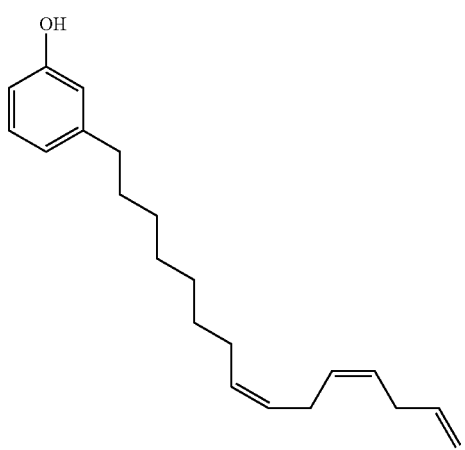 [SMILES: C=CC/C=C\C/C=C\CCCCCCCc1cccc(O)c1]

Figure 3:
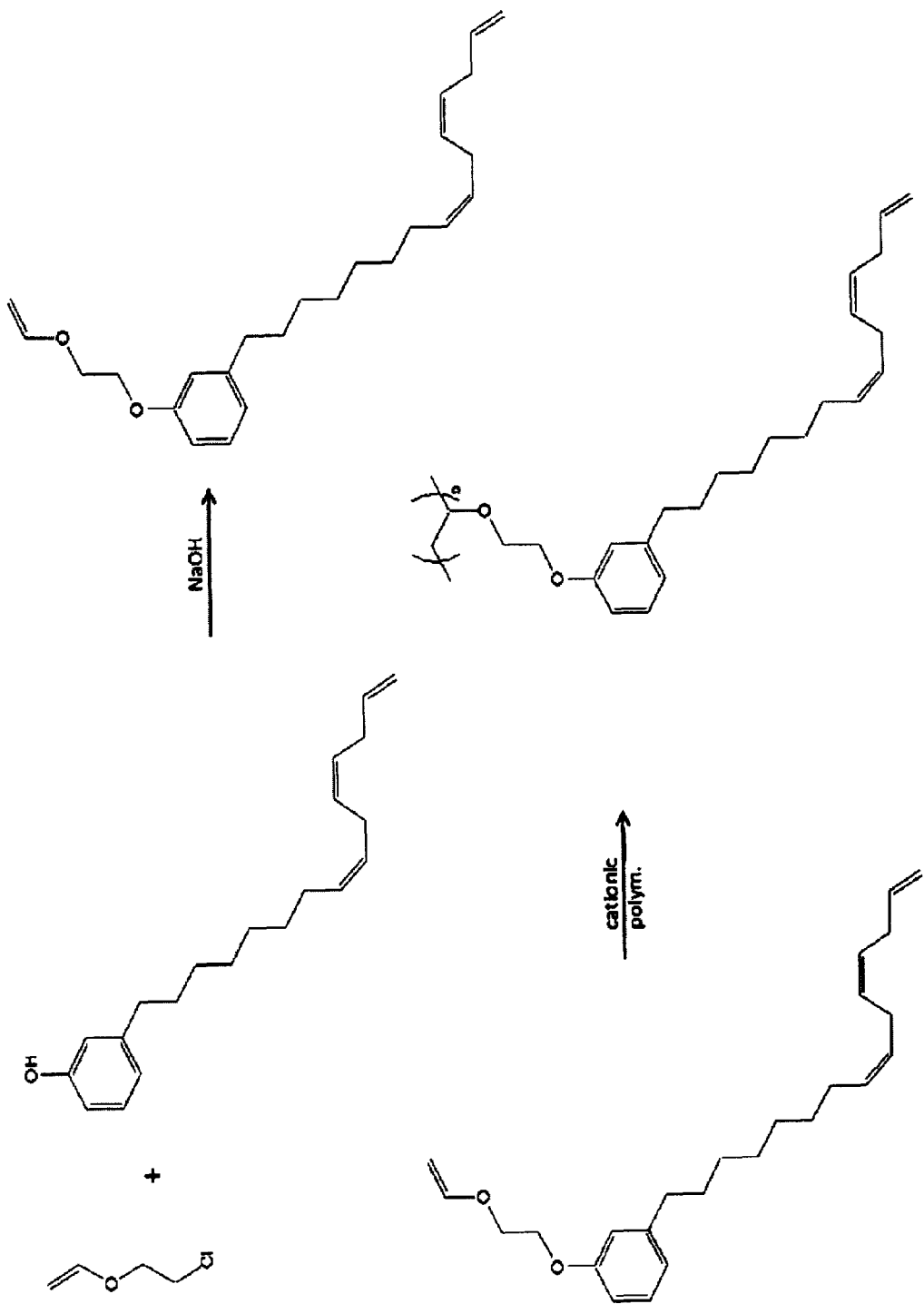
FIG. 3 shows synthesis of a cardanol-based vinyl ether monomer and polymer.

Cardanol can be obtained from Cardolite Corporation (Newark, N.J.). Since this compound has a phenolic group, it can be used to produce a vinyl ether monomer, for example by using Williamson ether synthesis. Analogous to the eugenol vinyl ether (AMB) described above, the monomer and polymer could be produced as shown in FIG. 3.

As with other plant oil-based vinyl ether monomers and the eugenol (AMB) and isoeugenol vinyl ether monomers, this cardanol-based vinyl ether monomer can be copolymerized with other monomers and the unsaturation can be used for crosslinking either directly or through derivatization. Alternatively, these monomers and polymers can be derivatized for other purposes besides crosslinking.

Example 19

Synthesis of the Vinyl Ether Monomer Based on Cardanol (i.e. Cardanolethyl Vinyl Ether)

A novel vinyl ether monomer was produced by the reaction of cardanol with 2-chloroethyl vinyl ether. This monomer will be referred to as cardanol ethyl vinyl ether (CEVE). A detailed description of the synthesis of CEVE is as follows: 50 g of cardanol (Cardolite Corporation, USA), 22 g of sodium hydroxide (>98.5%, AMRESCO LLC), and 300 ml of N,N-dimethylformamide (VWR, 99.8%) were combined in a 1 L, 2-neck round bottom flask. Nitrogen was purged for 10 minutes into the reaction mixture and 24 g of 2-chloroethyl vinyl ether (TCI Chemicals, >97%) was added to mixture. The reaction mixture was heated at 80° C. for 16 hours. Next, the reaction mixture was cooled to room temperature and diluted with 300 mL of n-hexane. The reaction mixture was washed two times with 300 mL of deionized (DI) water, two times with 100 mL of 2N potassium hydroxide solution in DI water, and one time with brine solution (200 mL). The hexane layer was dried with $MgSO_4$. The filtered solution was then passed through a silica column. The product was isolated by evaporation of volatiles at a temperature of 30° C. and a pressure of 5 millibar. Successful production of CHVE was determined using proton nuclear magnetic resonance spectroscopy ($^1H$ NMR). $^1H$ NMR (400 MHz, CDCl3, TMS): δ (ppm) 6.5-7.2 (m, 4H, Aromatic CH); 6.5-6.6 (dd, 1H, —OCH═$CH_2$); 4.9-5.5 (m, 2.5H, —$CH_2$CH═CH$CH_2$—; —$CH_2$CH═$CH_2$); 3.9-4.3 (m, 6H, —O$CH_2$$CH_2$O—; —OCH═$CH_2$); 2.7-2.9 (0.7H, ═CH$CH_2$CH═); 2.5-2.7 (t, 2H, Ar—$CH_2$$CH_2$$CH_2$—); 1.9-2.2 (m, 3.8H, ═CH$CH_2$$CH_2$—); 1.5-1.7 (m, 2H, Ar—$CH_2$$CH_2$$CH_2$—); 1.2-1.5 (m, 13H, —$CH_2$$CH_2$$CH_2$—); (m, 1.9H, —CH$CH_3$).

Example 20

Synthesis of Poly(Cardanol Ethyl Vinyl Ether)

Poly(cardanol ethyl vinyl ether) [poly(CEVE)] was synthesized from CEVE using carbocationic polymerization. Toluene, which was used as the solvent, was distilled over calcium hydride, and CEVE was dried with anhydrous magnesium sulfate just before use. 1-isobutoxyethyl acetate (IBEA) was synthesized and dried according to the procedure described by Aoshima and Higashimura (1). Ethyl aluminum sesquichloride (97%, Sigma-Aldrich) was diluted with the dry toluene to produce a 25 weight percent solution. The polymerization was carried out inside a dry nitrogen glove box using a 500 ml round-bottom flask equipped with an overhead stirrer. All glassware was dried at 200° C. for 2 hours before use. 30 g of dry CEVE and 190 mg of IBEA were dissolved in 150 mL of dry toluene and chilled to 0° C. In a 200 mL glass container, 1.95 mL of the coinitiator, $Et_3Al_2Cl_3$ (25 wt % in toluene), was added to 100 mL of dry toluene inside the glove box and the solution chilled to 0° C. The polymerization was initiated by addition of the coinitiator to the reaction mixture. The reaction was terminated after 2 hours by the addition of 300 mL of chilled methanol. Termination with this volume of methanol also caused the polymer to precipitate from solution. The polymer was isolated and subsequently purified by redissolving in toluene and reprecipitating in methanol three times. The purified polymer was stripped of residual methanol using a vacuum oven operating at 70-80 mm of Hg at 30° C. for 3 hours. The polymer yield was 95% and it was stored as a 50% solution in toluene.

Polymer molecular weight was characterized using a high-throughput Symyx Rapid Gel Permeation Chromatography System equipped with an evaporative light scattering detector (PL-ELS 1000). The number-average molecular weight and molecular weight distribution of the poly (CEVE), expressed relative to polystyrene standards, was 47,610 g/mole and 1.39, respectively.

Example 21

Coatings Derived from Poly(CEVE)

Free films and coatings of poly(CEVE) were prepared using anautoxidation catalyst system based on a mixture of cobalt 2-ethylhexanoate (12% Cobalt, OMG Americas), zirconium 2-ethylhexanoate (18% Zirconium, OMG Americas), and zinc carboxylate in mineral spirits (8% Zinc, OMG Americas). Table XXV provides the composition of the coating solution used to produce free film specimens and coatings. The solution was thoroughly blended for 30 seconds using a FlackTek mixer operating at 3500 rpm. The solution was coated on nine pretreated steel panels (Q-Panel stock number SP105337), three glass panels, and three Teflon®-laminated glass panels using a drawdown bar with an 8 mil gap. Cured specimens were produced three different temperatures, namely, room temperature, 120° C. for 1 hour, and 150° C. for 1 hour. These panels were then kept at room temperature for one week before carrying out characterization. Coating on the Teflon®-laminated glass panels allowed for free film samples to be produced for the characterization of mechanical and viscoelastic properties. The coated glass panels were used for pendulum hardness measurements.

TABLE XXV

The composition of the poly(CEVE) coating solution used to produce test specimens.

| Component | | | | |
|---|---|---|---|---|
| Poly(CEVE), g | Toluene, g | Cobalt octate, mg | Zirconium octate, mg | Nuxtra ® Zinc, mg |
| Weight 10 | 6 | 8 | 40 | 450 |

For mechanical property characterization, specimens were cut from free films using a dye that produced ASTM D-638 Type Vtensile specimens. Specimens for characterizing viscoelastic properties using dynamic mechanical analysis (DMA) were produced by using a rectangular specimen with dimensions of 17 to 20 mm in length, 5 mm in width, and 0.07 to 0.10 mm in thickness. For DMA, data was obtained over a temperature range of −50° C. to 150° C. at a heating rate 5° C./minute, frequency of 1 Hz, and strain amplitude of 0.01%. The glass-transition temperature (Tg) was reported as the temperature peak maximum from the tan δ versus temperature curve.

The coated steel panels were used to measure coating hardness, chemical resistance, flexibility, and impact resistance. Hardness was determined using the Konig pendulum hardness test (ASTM D4366-95), while chemical resistance was determined using the MEK double rub test (ASTM D5402-93). Coating flexibility was characterized using the conical mandrel bend test (ASTM D522), and impact resistance was characterized using the falling weight impact tester (ASTM D2794). For impact testing, the uncoated side of the panel received the impact (i.e. reverse impact). Table XXVI provides the data obtained for the poly(CEVE) coatings.

TABLE XXVI

Data obtained for cured coatings of poly(CEVE).

| | Poly (CEVE) Curing Temp (° C.) | | |
|---|---|---|---|
| Measurement | 25 | 120 | 150 |
| ASTM Testing of Coated Substrates | | | |
| Average thickness (μm) | 81 + 0 | 80 + 1 | 76 + 1 |
| König pendulum hardness (steel substrate), sec. | 37 + 1 | 38 + 0 | 41 + 1 |
| Cross hatch adhesion (steel substrate) | 3B + 0 | 4B + 0 | 4B + 0 |
| Conical mandrel bend test, Elongation % | 100 | 100 | 100 |
| Reverse impact (in-lb) | >172 | >172 | >172 |
| MEK double rubs | 120 + 10 | 120 + 7 | 150 + 15 |
| Tensile Testing of Free Film | | | |
| Young's modulus (MPa) | 18.9 + 1.3 | 20.9 + 1.3 | 46.2 + 1.9 |
| Elongation at Break (%) | 20.3 + 1.1 | 19.0 + 1.7 | 16.1 + 0.8 |
| Dynamic Mechanical Analysis of Free Films | | | |
| Storage modulus at 100° C. (MPa) | 8.2 | 9.5 | 11.2 |
| Tg from tanδ (° C.) | 5 | 11 | 13 |

Example 22

Synthesis of Copolymers of CEVE and Cyclohexyl Vinyl Ether (CHVE)

Poly(CEVE-co-CHVE) was synthesized from CEVE and CHVE monomers using carbocationic polymerization. As described in Table XXVII, two different copolymers were synthesized that differed with respect to the monomer feed ratio used for the polymerization. Just prior to the polymerization, toluene and CHVE were dried by distillation over calcium hydride, while CEVE was dried with anhydrous magnesium sulfate. Ethyl aluminum sesquichloride (97%, Sigma-Aldrich) was diluted with the dried toluene to produce a 25 weight percent solution. All glassware used for the polymerization was dried at 200° C. allowed to cool inside a glove equipped with a cold well. A representative procedure for the synthesis of poly(CEVE-co-CHVE)-75/25 inside a dry nitrogen glove box is as follows: To a 1000 mL round-bottom flask equipped with an overhead stirrer, 30 g of CEVE, 10 g of CHVE, and 211 mg of IBEA were dissolved in 200 mL of dry toluene and chilled to 0° C. In a 200 mL flask, 2.17 mL of ethyl aluminum sesquichloride (25 wt % in toluene) was added to 100 mL of dry toluene and chilled to 0° C. The polymerization was initiated by the rapid addition of the ethyl aluminum sesquichloride solution to the monomer solution. The reaction was terminated after 2 hours by the addition of 300 mL of chilled methanol. In addition to terminating the polymerization, the methanol addition caused precipitation of the copolymer. The polymer was isolated and subsequently purified by redissolving in toluene and reprecipitating in methanol three times. The purified polymer was stripped of residual methanol using a vacuum oven operating at 70-80 mm of Hg at 30° C. for 3 hours. The polymer was stored as a 50% solution in toluene. Polymer molecular weight was characterized using a high-throughput Symyx Rapid Gel Permeation Chromatography System equipped with an evaporative light scattering detector (PL-ELS 1000). The number-average molecular weight (Mn) and molecular weight distribution (MWD) of the poly(CEVE-co-CHVE) copolymers, expressed relative to polystyrene standards, are given in Table XXVII.

TABLE XXVII

Composition of the polymerization mixtures used to produce poly(CEVE-co-CHVE) copolymers.

| Sample ID | CEVE, g | CHVE, g | IBEA, mg | Et3Al2Cl3 (25 wt % in toluene), mL | Toluene, mL | Mn, g/mole | MWD |
|---|---|---|---|---|---|---|---|
| Poly (CEVE-co-CHVE)-75/25 | 30 | 10 | 211 | 2.17 | 300 | 43,500 | 1.42 |
| Poly (CEVE-co-CHVE)-50/50 | 20 | 20 | 169 | 1.74 | 300 | 40,500 | 1.65 |

Example 23

Coatings Based on Copolymers of CEVE and CHVE

Free films and coatings of the poly(CEVE-co-CHVE) copolymers were prepared using an autoxidation catalyst system based on a mixture of cobalt 2-ethylhexanoate (12% Cobalt, OMG Americas), zirconium 2-ethylhexanoate (18% Zirconium, OMG Americas), and zinc carboxylate in mineral spirits (8% Zinc, OMG Americas). Table XXVIII provides the composition of the coating solution used to produce free film specimens and coatings. The solution was thoroughly blended for 30 seconds using a FlackTek mixer operating at 3500 rpm. The solution was coated on nine pretreated steel panels (Q-Panel stock number SP105337), three glass panels, and three Teflon®-laminated glass panels using a drawdown bar with an 8 mil gap. Cured specimens were produced three different temperatures, namely, room temperature, 120° C. for 1 hour, and 150° C. for 1 hour. These panels were then kept at room temperature for one week before carrying out characterization. Coating on the Teflon®-laminated glass panels allowed for free film samples to be produced for the characterization of mechanical and viscoelastic properties. The coated glass panels were used for pendulum hardness measurements.

For mechanical property characterization, specimens were cut from free films using a dye that produced ASTM D-638 Type V tensile specimens. Specimens for characterizing viscoelastic properties using dynamic mechanical analysis (DMA) were produced by using a rectangular specimen with dimensions of 17 to 20 mm in length, 5 mm in width, and 0.07 to 0.10 mm in thickness. For DMA, data was obtained over a temperature range of −50° C. to 150° C. at a heating rate 5° C./minute, frequency of 1 Hz, and strain amplitude of 0.01%. The glass-transition temperature (Tg) was reported as the temperature peak maximum from the tan δ versus temperature curve.

The coated steel panels were used to measure coating hardness, chemical resistance, flexibility, and impact resistance. Hardness was determined using the Konig pendulum hardness test (ASTM D4366-95), while chemical resistance was determined using the MEK double rub test (ASTM D5402-93). Coating flexibility was characterized using the conical mandrel bend test (ASTM D522), and impact resistance was characterized using the falling weight impact tester (ASTM D2794). For impact testing, the uncoated side of the panel received the impact (i.e. reverse impact). Table XXVIX provides the data obtained for the poly(CEVE-co-CHVE)-based coatings.

TABLE XXVIII

The composition of the poly(CEVE-co-CHVE)-based coating solutions used to produce test specimens.

| Component | Poly(CEVE-co-CHVE) 75/25, g | Poly(CEVE-co-CHVE) 50/50, g | Touene, g | Cobalt octate, mg | Zirconium octate, mg | Nuxtra ® Zinc, mg |
|---|---|---|---|---|---|---|
| Poly (CEVE-co-CHVE) 75/25 | 10 | — | 6 | 8 | 40 | 450 |
| Poly (CEVE-co-CHVE) 50/50 | — | 10 | 6 | 8 | 40 | 450 |

TABLE XXVIX

Data obtained for coatings based on poly(CEVE-co-CHVE)-75/25 or poly(CEVE-co-CHVE)-50/50.

| | Measurement | | | | | |
|---|---|---|---|---|---|---|
| | Poly(CEVE-co-CHVE)-50/50 | | | Poly(CEVE-co-CHVE)-75/25 | | |
| | Curing Temp (° C.) | | | | | |
| | 25 | 120 | 150 | 25 | 120 | 150 |
| ASTM Testing of Coated Substrates | | | | | | |
| Average thickness (μm) | 70 + 1 | 70 + 1 | 69 + 1 | 72 + 1 | 72 + 1 | 71 + 1 |
| Konig pendulum hardness (steel substrate), sec. | 27 + 1 | 34 + 1 | 39 + 1 | 19 + 1 | 22 + 1 | 23 + 1 |
| Cross hatch adhesion (steel substrate) | 3B | 4B | 5B | 3B | 4B | 5B |
| Conical mandrel bend test, Elongation % | 100 | 100 | 100 | 100 | 100 | 100 |
| Reverse impact (in-lb) | >172 | >172 | >172 | >172 | >172 | >172 |
| MEK double rubs | 90 + 12 | 100 + 15 | 120 + 8 | 140 + 10 | 145 + 8 | 170 + 12 |
| Tensile Testing of Free Film Specimens | | | | | | |
| Young's modulus (MPa) | 6.4 + 0.8 | 9.5 + 0.8 | 10.6 + 1.1 | 12.6 + 0.4 | 13.5 + 0.6 | 18.3 + 0.9 |
| Elongation at Break (%) | 90.7 + 5.2 | 80.0 + 3.3 | 68.4 + 4.6 | 48.7 + 1.4 | 46.1 + 1.6 | 32.0 + 1.2 |
| Dynamic Mechanical Analysis of Free Films | | | | | | |
| Storage modulus at 120° C. (MPa) | 3.6 | 3.0 | 2.9 | 8.1 | 8.6 | 8.7 |
| Tg from tan δ (° C.) | 22.6 | 21 | 23.6 | 16.7 | 16.4 | 19 |

Example 24

Synthesis of Copolymers of CEVE and Maleic Anhydride (MA)

Poly (CEVE-co-MA) was synthesized from CEVE and MA using free radical polymerization. Just prior to the polymerization, toluene was dried by distillation over calcium hydride, while CEVE was dried with anhydrous magnesium sulfate. In a two neck 250 mL round bottom flask, 30 g of dry CEVE, 7.74 g of MA, and 754 mg of 2,2'-azobis (2-methylpropionitrile), were dissolved in 125 mL of dry toluene. The reaction mixture was purged with $N_2$ for 15 minutes. It was then placed in a 70° C. oil bath and kept under a nitrogen atmosphere. The polymerization was allowed to occur over a 3 hour period before the copolymer was precipitated by adding 300 mL of methanol. The copolymer was isolated and subsequently purified by redissolving in toluene and reprecipitating in methanol three times. The purified polymer was stripped of residual methanol using a vacuum oven operating at 70-80 mm of Hg at 30° C. for 3 hours. The polymer was stored as a 50% solution in toluene. The copolymer yield was 86%, and polymer molecular weight was characterized using a high-throughput Symyx Rapid Gel Permeation Chromatography System equipped with an evaporative light scattering detector (PL-ELS 1000). The number-average molecular weight and molecular weight distribution of the poly(CEVE-co-MA), expressed relative to polystyrene standards, was 17,900 g/mole and 1.84, respectively.

Example 25

Coatings Based on Copolymers of CEVE and MA

Free films and coatings of the poly(CEVE-co-MA) copolymer were prepared using an autoxidation catalyst system based on a mixture of cobalt 2-ethylhexanoate (12% Cobalt, OMG Americas), zirconium 2-ethylhexanoate (18% Zirconium, OMG Americas), and zinc carboxylate in mineral spirits (8% Zinc, OMG Americas). In addition, an analogous set of coatings were prepared without catalyst. Table XXX provides the composition of the coating solutions used to produce free film specimens and coatings. The solution was thoroughly blended for 30 seconds using a FlackTek mixer operating at 3500 rpm. The solution was coated on nine pretreated steel panels (Q-Panel stock number SP105337), three glass panels, and three Teflon®-laminated glass panels using a drawdown bar with an 8 mil gap. Cured specimens were produced three different temperatures, namely, room temperature, 120° C. for 1 hour, and 150° C. for 1 hour. These panels were then kept at room temperature for one week before carrying out characterization. Coating on the Teflon®-laminated glass panels allowed for free film samples to be produced for the characterization of mechanical and viscoelastic properties. The coated glass panels were used for pendulum hardness measurements.

For mechanical property characterization, specimens were cut from free films using a dye that produced ASTM D-638 Type V tensile specimens. Specimens for characterizing viscoelastic properties using dynamic mechanical analysis (DMA) were produced by using a rectangular specimen with dimensions of 17 to 20 mm in length, 5 mm in width, and 0.07 to 0.10 mm in thickness. For DMA, data was obtained over a temperature range of −50° C. to 150° C. at a heating rate 5° C./minute, frequency of 1 Hz, and strain amplitude of 0.01%. The glass-transition temperature (Tg) was reported as the temperature peak maximum from the tan δ versus temperature curve.

The coated steel panels were used to measure coating hardness, chemical resistance, flexibility, and impact resistance. Hardness was determined using the König pendulum hardness test (ASTM D4366-95), while chemical resistance was determined using the MEK double rub test (ASTM D5402-93). Coating flexibility was characterized using the conical mandrel bend test (ASTM D522), and impact resistance was characterized using the falling weight impact tester (ASTM D2794). For impact testing, the uncoated side of the panel received the impact (i.e. reverse impact). Table XXXI provides the data obtained for the poly(CEVE-co-MA)-based coating produced with the autoxidation catalyst package, while Table XXXII provides data for coatings produced without the use of the catalyst package.

TABLE XXX

The composition of coating solutions derived from the poly(CEVE-co-MA) copolymer.

| | Component | | | | |
|---|---|---|---|---|---|
| | poly(CEVE-co-MA), g | Toluene, g | Cobalt octate, mg | Zirconium octate, mg | Nuxtra ® Zinc, mg |
| poly(CEVE-co-MA) | 10 | 6 | 4 | 20 | 225 |
| poly(CEVE-co-MA) without catalyst | 10 | 6 | — | — | — |

TABLE XXXI

Data obtained for cured coatings of poly(CEVE-co-MA) with catalyst.

| | poly(CEVE-co-MA) Curing temp (° C.) | | |
|---|---|---|---|
| Measurement | 25 | 120 | 150 |
| ASTM Testing of Coated Substrates | | | |
| Average thickness (μm) | 48 + 1 | 48 + 1 | 48 + 1 |
| König pendulum hardness (steel substrate), sec. | 92 + 2 | 126 + 2 | 152 + 1 |
| Cross hatch adhesion (steel substrate) | 5B | 5B | 5B |
| Conical mandrel bend test, Elongation % | 100 | 100 | 100 |
| Reverse impact (in-lb) | 152 | 128 | 48 |
| MEK double rubs | 80 + 5 | 190 + 10 | 1180 + 10 |
| Tensile Testing of Free Film Specimens | | | |
| Young's modulus (MPa) | 745 + 17 | 950 + 20 | 1262 + 13 |
| Elongation at Break (%) | 12.5 + 0.8 | 10.7 + 0.6 | 8.4 + 1.1 |
| Dynamic Mechanical Analysis of Free Films | | | |
| Storage modulus at 150° C. (MPa) | 16 | 21 | 37 |
| Tg from tanδ (° C.) | 108 | 115 | 123 |

TABLE XXXII

Data obtained for cured coatings of poly(CEVE-co-MA) without catalyst.

| | poly(CEVE-co-MA) Curing temp (° C.) | | |
|---|---|---|---|
| Measurement | 25 | 120 | 150 |
| ASTM Testing of Coated Substrates | | | |
| Average thickness (μm) | 50 + 2 | 50 + 2 | 50 + 2 |
| König pendulum hardness (steel substrate), sec. | 32 + 2 | 96 + 2 | 128 + 2 |
| Cross hatch adhesion (steel substrate) | 5B | 5B | 5B |
| Conical mandrel bend test, Elongation % | 100 | 100 | 100 |
| Reverse impact (in-lb) | >172 | >172 | 72 |
| MEK double rubs | 80 + 5 | 170 + 10 | 210 + 10 |
| Tensile Testing of Free Film Specimens | | | |
| Young's modulus (MPa) | 139 + 4 | 650 + 16 | 1004 + 18 |
| Elongation at Break (%) | 30.0 + 2.1 | 20.0 + 1.6 | 10.0 + 1.0 |
| Dynamic Mechanical Analysis of Free Films | | | |
| Storage modulus at 150° C. (MPa) | — | 8.6 | 10.0 |
| Tg from tanδ (° C.) | — | 89 | 111 |

Example 26

Synthesis of a Vinyl Ether Monomer from Vanillin 3 g of vanillin (0.019 mole) and 0.997 g of sodium hydroxide (0.025 mole) was added to 10 mL of distilled dimethylformamide in a 50 mL two-neck, round-bottom flask that was equipped with an oil bath, magnetic stir bar, and nitrogen blanket. Next, 2.13 g of 2-chloroethyl vinyl ether (0.02 mole) was added slowly to the reaction mixture and the temperature was raised to 70° C. The reaction was carried out for 5 hr. To isolate the product, 15 mL of deionized (DI) water was added to the reaction mixture and the solution was extracted with 50 ml of dichloromethane twice. The two dichloromethane layers were combined and then washed with 15 ml DI water and then with 10 mL of an aqueous potassium hydroxide (10% w/v)) solution. The dichloromethane layer was then dried with anhydrous magnesium sulfate. The suspension was clarified by filtration and the solvent was removed under reduced pressure to yield vanillin vinyl ether monomer as a white powder. The material was further purified by crystallization from hexane. The structure of the vinyl ether monomer from vanillin was confirmed by proton nuclear magnetic resonance spectroscopy: $^1$H NMR (400 MHz, CDCl$_3$): δ 9.85 (s, 1H), δ 7.40-7.44 (m, 2H), δ 7.02 (d, 1H), δ 6.51-6.56 (dd, 1H), δ 4.35-4.36 (t, 2H), δ 4.21-4.26 (dd, 1H), δ 4.10-4.12 (t, 2H), δ 4.0-4.08 (dd, 1H), δ 3.92 (s, 1H).

The complete disclosures of all patents, patent applications including provisional patent applications, publications including patent publications and nonpatent publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A compound comprising 1-(2-(4-allyl-2-methoxyphenoxy)ethoxy)ethyl acetate.

2. A method for making the compound of claim 1, the method comprising
contacting 4-allyl-2-methoxy-1-(2-(vinyloxy)ethoxy) benzene with acetic acid under conditions and for a time sufficient to yield the compound of claim 1.

3. A method for making a functionalized polymer or copolymer comprising:
contacting at least one vinyl ether monomer with the compound of claim 1 under conditions and for a time sufficient to yield the functionalized polymer or copolymer, wherein the functionalized polymer or copolymer comprises a terminal allyl group.

4. The method of claim 3 comprising contacting at least one vinyl ether monomer and at least one additional monomer with the 1-(2-(4-allyl-2-methoxyphenoxy)ethoxy)ethyl acetate under conditions and for a time sufficient to yield the allyl-functionalized polymer or copolymer.

5. The method of claim 3 further comprising reacting the allyl-functionalized polymer or copolymer with at least one second polymer or copolymer, to yield a block or graft copolymer produced through a reaction at the terminal allyl group of the functionalized polymer or copolymer.

6. The method of claim 5 wherein the block or graft copolymer comprises a poly(dimethylsiloxane) (PDMS).

\* \* \* \* \*